US011319568B2

(12) United States Patent
Wu et al.

(10) Patent No.: US 11,319,568 B2
(45) Date of Patent: *May 3, 2022

(54) METHODS FOR INCREASING MANNOSE CONTENT OF RECOMBINANT PROTEINS

(71) Applicant: AMGEN INC., Thousand Oaks, CA (US)

(72) Inventors: Jian Wu, Acton, MA (US); Sean Davern, Seattle, WA (US); Simina Crina Petrovan, Wakefield, MA (US); Michael Charles Brandenstein, Woodinville, WA (US); Katherine Rose Lindahl, Somerville, MA (US); Shawn Erik Lillie, Puyallup, WA (US)

(73) Assignee: AMGEN INC., Thousand Oaks, CA (US)

( * ) Notice: Subject to any disclaimer, the term of this patent is extended or adjusted under 35 U.S.C. 154(b) by 120 days.

This patent is subject to a terminal disclaimer.

(21) Appl. No.: 16/654,933

(22) Filed: Oct. 16, 2019

(65) Prior Publication Data

US 2020/0087698 A1 Mar. 19, 2020

Related U.S. Application Data

(63) Continuation of application No. 15/652,138, filed on Jul. 17, 2017, now abandoned, which is a continuation of application No. 14/776,404, filed as application No. PCT/US2014/022738 on Mar. 10, 2014, now Pat. No. 9,822,388.

(60) Provisional application No. 61/784,639, filed on Mar. 14, 2013.

(51) Int. Cl.
C12P 21/00 (2006.01)
C12N 5/00 (2006.01)
C12N 1/38 (2006.01)
C07K 16/00 (2006.01)

(52) U.S. Cl.
CPC ............ *C12P 21/005* (2013.01); *C07K 16/00* (2013.01); *C12N 1/38* (2013.01); *C12N 5/0037* (2013.01); *C07K 2317/14* (2013.01); *C07K 2317/41* (2013.01); *C12N 2500/32* (2013.01); *C12N 2500/34* (2013.01); *C12N 2510/02* (2013.01)

(58) Field of Classification Search
None
See application file for complete search history.

(56) References Cited

U.S. PATENT DOCUMENTS

| | | |
|---|---|---|
| 4,695,623 A | 9/1987 | Stabinsky |
| 4,897,471 A | 1/1990 | Stabinsky |
| 4,968,607 A | 11/1990 | Dower et al. |
| 5,075,222 A | 12/1991 | Hannum et al. |
| 5,149,792 A | 9/1992 | Thomason |
| 5,272,064 A | 12/1993 | Thomason |
| 5,395,760 A | 3/1995 | Smith et al. |
| 5,610,279 A | 3/1997 | Brockhaus et al. |
| 5,767,064 A | 6/1998 | Sims et al. |
| 5,856,296 A | 1/1999 | Mosley et al. |
| 5,981,713 A | 11/1999 | Colotta et al. |
| 6,015,938 A | 1/2000 | Boyle et al. |
| 6,096,728 A | 8/2000 | Collins et al. |
| 6,204,363 B1 | 3/2001 | Zsebo et al. |
| 6,235,883 B1 | 5/2001 | Jakobovits et al. |
| 6,271,349 B1 | 8/2001 | Dougall et al. |
| 6,337,072 B1 | 1/2002 | Ford et al. |
| 6,544,424 B1 | 4/2003 | Shevitz |
| 7,332,303 B2 * | 2/2008 | Schilling .......... C07K 14/70521 435/69.7 |
| 8,354,105 B2 | 1/2013 | Wu et al. |
| 2004/0115768 A1 * | 6/2004 | Follstad ................ C12P 21/005 435/69.1 |
| 2012/0276631 A1 * | 11/2012 | Bengea .................. C07K 16/00 435/404 |

FOREIGN PATENT DOCUMENTS

| | | |
|---|---|---|
| EP | 0183350 A2 | 6/1986 |
| EP | 0367566 B1 | 5/1997 |
| EP | 0460846 B1 | 2/2002 |
| JP | H06 292592 A | 10/1994 |
| WO | 1994/10308 A1 | 5/1994 |
| WO | 1994/028391 A1 | 12/1994 |
| WO | 1997/001633 A1 | 1/1997 |
| WO | 1999/028455 A1 | 6/1999 |
| WO | 2001/036637 A1 | 5/2001 |
| WO | 2004/008100 A2 | 1/2004 |
| WO | 2012/145682 A1 | 10/2012 |
| WO | 2012/149197 A2 | 11/2012 |
| WO | 2013/006479 A2 | 1/2013 |

OTHER PUBLICATIONS

Ahn et al., Effect of Culture Temperature on Erythropoietin Production and Glycosylation in a Perfusion Culture of Recombinant CHO Cells, Biotechnol. Bioeng (2008) 101:1234-1244.
Brasel et al., Hematologic Effects of flt3 Ligand In Vivo in Mice, Blood (1996) 88:2004-2012.
Do et al., Mechanism of BLyS Action in B Cell Immunity, Cytokine Growth Factor Rev. (2002), 13:1; 19-25.
Efren et al., Effects of Cell Culture Conditions on Antibody N-Linked Glycosylation—What Effects High Mannose 5 Glycoform, Biotechnol. Bioeng (2011) 108(10):2348-2358.
Goetze et al., High-Mannose Glycans on the FcRegion of the Therapeutic IgG Antibodies Increase Serum Clearance in Humans, Glycobiology (2011), 21:949-959.
Grammer et al., Modulation of Antibody Galactosylation Through Feeding of Uridine, Manganese Chloride, and Galactose, Biotechnol. Bioeng (2011) 108(7):1591-1602.

(Continued)

*Primary Examiner* — Allison M Fox

(57) ABSTRACT

The present invention relates to methods of modulating the mannose content of recombinant proteins.

23 Claims, 32 Drawing Sheets

(56) References Cited

OTHER PUBLICATIONS

Hakansson et al., Crystal Structure of the Trimeric α-Helical Coiled-Coil and the Three Lectin Domains of Human Lung Surfactant Protein D, Structure (1999), 7:255-64.

Harbury et al., a Switch Between Two-, Three-, and Four-Stranded Coiled Coils in GCN4 Leucine Zipper Mutants, Science (1993), 262:1401-05.

Harbury et al., Crystal Structure of an Isoleucine-Zipper Trimer, Nature (1994), 371:80-83.

Hills et al., Metabolic Control of Recombinant Monoclonal Antibody N-Glycosylation in GS-NSO Cells, Biotechnol Bioeng (2001) 75(2):239-251.

Hubbard et al., Synthesis and Processing of Asparagine-Linked Oligosaccharides, *Ann. Rev. Biochem.* (1981) 50:55-583.

James et al., Glucose Starvation Alters Lipid-Linked Oligosaccharide Biosynthesis in Chinese Hamster Ovary Cells, *The Journal of Biological Chemistry* (1981) 256(12):6255-6261.

Kaufman et al., Synthesis, Processing, and Secretion of Recombinant Human Factor VIII Expressed in Mammalian Cells, J. Biol Chem (1988) 263:6352-6362.

Kaufman, Selection and Coamplification of Heterologous Genes in Mammalian Cells, Meth Enzymol (1990)185:537-566.

Lovejoy et al., Crystal Structure of a Synthetic Triple-Stranded α-Helical Bundle, Science (1993), 259:1288-1293.

Maisonpierre et al., Angiopoietin-2, a Natural Antagonist for Tie2 That Disrupts in vivo Angiogenesis, Science (1997) 277:5322; 55-60.

McKinnon et al., Expression, Purification and Characterization of Secreted Recombinant Human Insulin-Like Growth Factor-I (IGF-I) and the Potent Variant des(1-3)IGF-I in Chinese Hamster Ovary Cells, *J. Mol. Endocrinol.* (1991) 6 :231-239.

NCBI Accession No. NM_00682.

Ruegg et al., Sequence of Human Transcript Expressed in T-Lymphocytes and Encoding a Fibrinogen-Like Protein, Gene (1995) 160:257-262.

Schmelzer et al., Hyperosmotic Stress and Elevated $pCO_2$ Alter Monoclonal Antibody Charge Distribution and Monosaccharide Content, *Biotechnol. Bioeng.* (2002) 77(4).

Schmelzer et al., Effects of Osmoprotectant Compounds on NCAM Polysialylation Under Hyperosmotic Stress and Elevated $pCO_2$, *Biotechnol. Prog.* (2002) 18 346-353.

Stettler, et al., New Disposable Tubes for Rapid and Precise Biomass Assessment for Suspension Cultures of Mammalian Cells, Biotechnol Bioeng. (2006) 95(6):1228-1233.

Urlaub et al., Isolation of Chinese Hamster Cell Mutants Deficient in Dihydrofolate Reductase Activity, Proc Natl Acad Sci USA (1980) 77:4216-4220.

Voisard et al., Potential of Cell Retention Technques for Large-Scale High Density Perfusion Culture of Suspended Mammalian Cells, Biotechnol. Bioeng. (2003), 82:751-765.

Wong et al., Impact of Dynamic Online Fed-Batch Strategies on Metabolism, Productivity and N-Glycosylation Quality in CHO Cell Cultures, *Biotechnol. & Bioeng.*, Wiley & Sons, NJ (2005) 89(2):164-177.

Wood et al., High Level Synthesis of Immunoglobulins in Chinese Hamster Ovary Cells, (1990), J. Immunol. (1990) 145:3011-3016.

Yu et al., Production, Characterization and Pharmacokinetic Properties of Antibodies with N-Linked Mannose-5 Glycans, *MAbs* (2012), 4 :475-487.

\* cited by examiner

METHODS FOR INCREASING MANNOSE CONTENT OF RECOMBINANT PROTEINS

CROSS-REFERENCE TO RELATED APPLICATIONS

This application is a continuation of U.S. patent application Ser. No. 15/652,138 filed Jul. 17, 2017, which is a continuation of Ser. No. 14/776,404, filed Sep. 14, 2015, which is a National Stage application under 35 U.S.C. § 371 of International Application No. PCT/US2014/022738 (which designated the United States), having an international filing date of Mar. 10, 2014, which claims the benefit of U.S. Provisional Application No. 61/784,639 filed Mar. 14, 2013, which is incorporated herein by reference in its entirety.

BACKGROUND OF INVENTION

IgG antibodies produced in mammalian cell cultures may contain varied levels of high mannose (HM) glycoforms such as Mannose5 (Man5), Mannose6 (Man6), Mannose7 (Man7), Mannose8 (Man8) and Mannose9 (Man9). High mannose glycoform content of therapeutic proteins and antibodies is a critical quality attribute that has been found to affect pharmacokinetic properties of certain therapeutic antibodies (Goetze, et al., (2011) *Glycobiology* 21, 949-59; Yu, et al., (2012) *MAbs* 4, 475-87).

Glycoforms of an antibody expressed by Chinese hamster ovary (CHO) host cell are largely determined during cell line generation and clone selection. However, HM content can also be affected by cell culture conditions (Pacis, et al., (2011) *Biotechnol Bioeng* 108, 2348-2358). It is common in therapeutic antibody industry to seek a desired range of HM content for an antibody product due to process changes, scale-up, improvements or the need to match existing antibody quality attributes. So far, methods applied for manipulating HM content of an antibody in cell culture include changes in media compositions, osmolality, pH, temperature, etc (Yu, et al., supra, Pacis et al., supra, Chee Furng Wong et al., (2005) *Biotechnol Bioeng* 89, 164-177; Ahn, et al., (2008) *Biotechnol Bioeng* 101, 1234-44). The effectiveness of these methods is specific to cell lines, molecule types and media environment. Additionally these methods tend to also alter antibody productivity, cell culture behavior and other antibody quality attributes. The effectiveness of these methods is obtained empirically.

Therefore, there is a need for a method to modulate the high mannose glycoform content of therapeutic proteins and antibodies. The invention provides a method for increasing the high mannose glycoform content through limited glucose in combination with an alternative carbon source.

SUMMARY OF THE INVENTION

The invention provides a method for modulating one or more high mannose glycan species on a recombinant protein during a mammalian cell culture process comprising limiting the amount of glucose in the cell culture medium and supplementing the cell culture medium with galactose or sucrose.

In one embodiment the glucose concentration in the cell culture medium is sufficient to result in a concentration of glucose in the spent medium at or about 0 g/L.

In one embodiment the concentration of glucose in the cell culture medium is from 0 to 8 g/L. In related embodiments the concentration of glucose in the cell culture medium is from 4 to 6 g/L; 1 to 3 g/L; 2 to 3 g/L; 2.5 g/L or 0 g/L.

In one embodiment the concentration of galactose in the cell culture medium is from 10 to 20 g/L. In related embodiments the concentration of galactose is from 10 to 15 g/L; 10 to 12 g/L or 11.5 g/L.

In one embodiment the concentration of sucrose in the cell culture medium is from 1 to 48 g/L. In a related embodiment the concentration of sucrose in the cell culture medium is from 16 to 24 g/L.

In one embodiment the limiting amount of glucose is added during a production phase.

In one embodiment the high mannose glycan species is mannose 5.

In one embodiment the cell culture process is a perfusion process.

The invention also provides a method for modulating one or more high mannose glycan species on a recombinant protein during mammalian cell culture comprising; establishing a mammalian cell culture in a bioreactor with a serum-free defined culture medium containing 5-8 g/L glucose; growing the mammalian cells during a growth phase and supplementing the culture medium with bolus feeds of a serum-free defined feed medium having from 5-8 g/L glucose; initiating a production phase in the cell culture by perfusion with a serum-free perfusion medium having 5-15 g/L glucose; at a predetermined time point, perfusing the cell culture with a low glucose perfusion medium containing or supplemented with a decreased amount of glucose, wherein said perfusion medium further contains or is supplemented with galactose.

In one embodiment the decreased amount of glucose is sufficient to result in a concentration of glucose in the spent medium of at or about 0 g/L.

In one embodiment the concentration of the decreased amount of glucose in the low glucose perfusion medium is from 0 to 3 g/L. In related embodiments the concentration of the decreased amount of glucose in the low glucose perfusion medium is from 2 to 3 g/L; 2.5 g/L or 0 g/L.

In one embodiment the concentration of galactose in the perfusion medium is from 10 to 20 g/L. In related embodiments the concentration of galactose in the low glucose perfusion medium is from 10 to 15 g/L; 10 to 12 g/L or 11.5 g/L.

In one embodiment perfusion begins on or about day 5 to on or about day 9 of the cell culture. In a related embodiment perfusion begins on or about day 5 to on or about day 7 of the cell culture. In another related embodiment perfusion begins when the cells have reached a production phase.

In another embodiment perfusion comprises continuous perfusion. In a related embodiment the rate of perfusion is constant.

In one embodiment perfusion is performed at a rate of less than or equal to 1.0 working volumes per day. In a related embodiment perfusion is performed at a rate that increases during the production phase from 0.25 working volume per day to 1.0 working volume per day during the cell culture. In another related embodiment perfusion is performed at a rate that reaches 1.0 working volume per day on day 9 to day 11 of the cell culture. In another related embodiment perfusion is performed at a rate that reaches 1.0 working volume per day on day 10 of the cell culture.

In one embodiment the bolus feeds of serum-free feed medium begin on day 3 or day 4 of the cell culture.

In one embodiment the mammalian cell culture is established by inoculating the bioreactor with at least $0.5 \times 10^6$ to 3.0×10⁶ cells/mL in a serum-free culture medium. In a related embodiment the mammalian cell culture is established by inoculating the bioreactor with at least 0.5×10⁶ to 1.5×10⁶ cells/mL in a serum-free culture medium.

In one embodiment the high mannose glycan species is Mannose 5.

In one embodiment the method described above further comprises temperature shift from 36° C. to 31° C.

In one embodiment the method described above further comprises a temperature shift from 36° C. to 33° C. In a related embodiment the temperature shift occurs at the transition between the growth phase and production phase. In a related embodiment the temperature shift occurs during the production phase.

In one embodiment the method above further comprising inducing cell growth-arrest by L-asparagine starvation followed by perfusion with a serum-free perfusion medium having an L-asparagine concentration of 5 mM or less. In a related embodiment the concentration of L-asparagine in the serum-free perfusion medium is less than or equal to 5 mM. In a related embodiment the concentration of L-asparagine in the serum-free perfusion medium is less than or equal to 4.0 mM. In another related embodiment the concentration of L-asparagine in the serum-free perfusion medium is less than or equal to 3.0 mM. In another related embodiment the concentration of L-asparagine in the serum-free perfusion medium is less than or equal to 2.0 mM. In another related embodiment the concentration of L-asparagine in the serum-free perfusion medium is less than or equal to 1.0 mM. In yet another related embodiment the concentration of L-asparagine in the serum-free perfusion medium is 0 mM. In yet another related embodiment the L-asparagine concentration of the cell culture medium is monitored prior to and during L-asparagine starvation.

In one embodiment the method above, further comprises that the packed cell volume during a production phase is less than or equal to 35%. In a related embodiment the packed cell volume is less than or equal to 35%. In a related embodiment the packed cell volume is less than or equal to 30%.

In one embodiment the viable cell density of the mammalian cell culture at a packed cell volume less than or equal to 35% is 10×10⁶ viable cells/ml to 80×10⁶ viable cells/ml. In a related embodiment the viable cell density of the mammalian cell culture is 20×10⁶ viable cells/ml to 30×10⁶ viable cells/ml.

In one embodiment the perfusion is accomplished by alternating tangential flow. In a related embodiment the perfusion is accomplished by alternating tangential flow using an ultrafilter or a microfilter.

In one embodiment the bioreactor has a capacity of at least 500 L. In a related embodiment the bioreactor has a capacity of at least 500 L to 2000 L. In a related embodiment the bioreactor has a capacity of at least 1000 L to 2000 L.

In one embodiment the mammalian cells are Chinese Hamster Ovary (CHO) cells.

In one embodiment the recombinant protein is selected from the group consisting of a human antibody, a humanized antibody, a chimeric antibody, a recombinant fusion protein, or a cytokine.

In one embodiment the method above further comprises a step of harvesting the recombinant protein produced by the cell culture.

In one embodiment the recombinant protein produced by the cell culture is purified and formulated in a pharmaceutically acceptable formulation.

In one embodiment the recombinant protein production in the high mannose glycan species are increased compared to a culture where the cells are not subjected to limited glucose in combination with galactose.

In one embodiment the concentration of the perfusion medium is 15 g/L.

DETAILED DESCRIPTION OF THE INVENTION

Figure 1A:
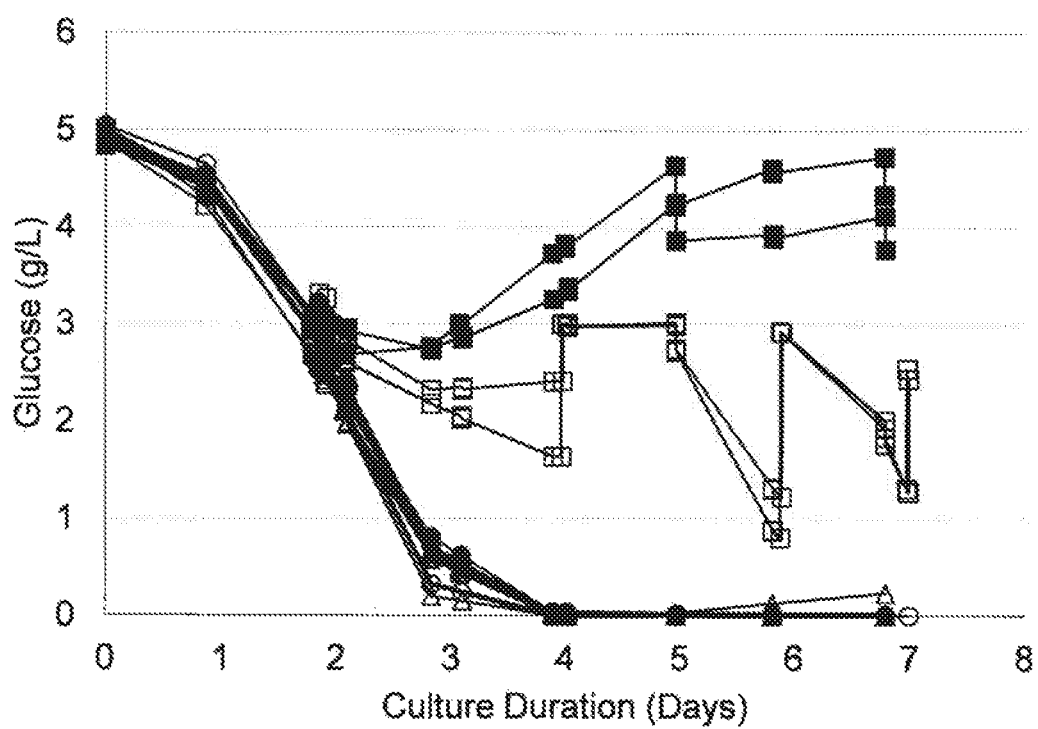
FIG. 1. Cell culture and Man5 profiles in a fed-batch process. (A) Glucose concentration g/L in culture supernatant. (B) Galactose concentration g/L in culture supernatant. (C) Viable Cell Density. (D) Viability. (E) Titer. (F) Man5. Glucose 1 g/L, galactose 0 g/L (open triangle). Glucose 1 g/L, galactose 4 g/L (solid triangle). Glucose 2 g/L, galactose 0 g/L (open circle). Glucose 2 g/L, galactose 4 g/L (solid triangle). Glucose 3 g/L, galactose 0 g/L (open square). Glucose 3 g/L, galactose 4 g/L (solid square).

Production of consistent and reproducible recombinant glycoprotein glycoform profiles remains a considerable challenge to the biopharmaceutical industry. Variations in cell culture processes play a significant role in antibody glycosylation profiles. Potential variability in the cell culture process physicochemical environment including pH, temperature, cell culture media composition, raw material lot-to-lot variation, medium filtration material, bioreactor scale difference, gassing strategy (air, oxygen, carbon dioxide) are just a few examples that can potentially alter glycosylation profiles.

It was observed that under conditions of low or limited glucose, the high mannose glycoform content of the recombinant protein increased, however, attributes of the cell culture, such as volumetric productivity, cell viability, and/or density, diminished. Increasing the glucose concentration improved the culture attributes, but decreased the high mannose glycoform content.

The invention provides a method for increasing high mannose glycoforms, in particular, Mannose5 (Man5), to achieve desired product quality attributes while maintaining desirable levels of certain cell culture parameters such as volumetric productivity, cell viability, and/or density, through the use of low or limited concentrations of glucose in combination with an alternate carbon source, in particular, galactose or sucrose. As described herein, culturing cells in a cell culture medium where glucose is limited by lowering the concentration of glucose in the cell culture medium, in combination with an alternative carbon source, resulted in a recombinant protein having am increased concentration of high mannose glucoforms, while maintaining cell growth, viability and titer at acceptable levels.

During the production phase of a cell culture, desirable culture parameters, such as viable cell density, cell viability, percent packed cell volume, titer and/or packed cell volume adjusted titer can be established by feeding the cell culture a cell culture medium containing sufficient glucose (from 5 g/L to 15 g/L or more) to establish and maintain these parameters. At such time during the cell culture production run, when it is desirable to increase the high mannose glycoform content of the recombinant protein being produced, the cell culture is then fed with a cell culture medium wherein the concentration of glucose is reduced such that will result in the desired increase in high mannose content. Such a cell culture medium is characterized by a lower concentration of glucose (0-8 g/L) in combination an alternative carbon source, such as galactose or sucrose.

Factors that determine the degree to which the glucose concentration will need to be lowered include which alternate carbon source used and how much is used; the cell culture production process; the cell type and mass and the glucose consumption. The greater the cell mass in the bioreactor, the greater the glucose consumption by the cell culture and hence the greater the amount of glucose that can be fed while still maintaining a limited glucose state that will produce the desired increase Man5 glycoform concentration. The manner in which the glucose is fed to the cell culture can also influence the amount of glucose necessary to maintain a limited glucose state that will produce the desired increase Man5 glycoform concentration. For example, in a fed-batch cell culture, glucose can be formulated into the cell culture medium and supplemented by bolus feeds. In a perfusion cell culture process, glucose concentration will depend on the feed rate (g/L/day) of the perfusion medium. Examples of both are provided herein. In addition, the amount of glucose in the culture medium during production can be measured, such as by spent media analysis for perfusion cultures. It was observed that Man5 levels increased when the amount of glucose in the spent medium was at or nearly 0 g/L.

High mannose glycoform production was increased when situations where glucose concentrations were decreased. However, low levels of glucose can impact the production of recombinant proteins in cell culture systems. Volumetric production, cell viability and viable cell density can all be negatively impacted in situations when glucose is limited. It was found that the addition of an alternate carbon source, such as galactose, to cell culture during a period of low or limited glucose was not slowed or stabilized the decreases in volumetric production, cell viability and viable cell density, while preserving the increased Man5 glycoforms. Alternatively, during a period of low or limited glucose, sucrose was also able to promote high mannose glycoform production, freeing some glucose to maintain volumetric production, cell viability and viable cell density. While cells could consume galactose, they did not consume sucrose in a limited glucose situation. It is believed that sucrose has an osmolality-related effect on cell metabolism and glycosylation of the molecule. Having the ability to manipulate and maintain the high mannose glycoform content of a recombinant protein during cell culture while minimizing product titer loss and maintaining cell viability represents a valuable and easily-implemented method for commercial therapeutic protein production.

Provided herein is a method of culturing mammalian cells that is useful for increasing high mannose glycoforms, in particular, Man 5, to achieve desired product quality attributes while maintaining acceptable product titer and cell viability by making use of a limiting amount of glucose in combination with an alternate carbon source, in particular, galactose or sucrose. The method provides culturing mammalian cells during growth and/or production phases in a cell culture medium having a high, non-limiting glucose concentration, from 5 to 15 g/L glucose, either compounded into the medium formulation, supplemented through bolus or continuous feeds or both. When viable cell density, cell viability and/or titer reach desired levels, the amount of glucose in the cell culture medium is lowered to a limiting amount, such that in the perfusion medium feed for example, the amount of glucose measured in spent medium is at or just above 0 g/L. The rate of glucose consumption is determined by the rate of glucose addition and/or the mass of the cell culture. Glucose can be fed at up to 8 g/L. In one embodiment, glucose is fed up to 6 g/L. In another embodiment glucose is fed up to 4 g/L. In another embodiment, glucose is fed up to 3 g/L. In another embodiment glucose is fed up to 2-3 g/L. In yet another embodiment glucose is fed up to 2.5 g/L. In another embodiment, glucose is 0 g/L.

In combination with the lowered glucose concentration, the cell culture medium contains or is supplemented with galactose, at a concentration up to 20 g/L. In one embodiment the concentration of galactose is from 10 to 15 g/L. In another embodiment the concentration of galactose is 11.5 g/L.

In another embodiment, in combination with the lowered glucose concentration, the cell culture medium contains or is supplemented with sucrose, at a concentration up to 48 g/L. In one embodiment the concentration of sucrose is 16 to 24 g/L.

Carbohydrate moieties are described herein with reference to commonly used nomenclature for oligosaccharides. A review of carbohydrate chemistry which uses this nomenclature can be found, for example, in Hubbard and Ivatt, Ann. Rev. Biochem. 50:555-583 (1981). This nomenclature includes, for instance, Man, which represents mannose; Gal which represents galactose; and Glc, which represents glucose.

By "cell culture" or "culture" is meant the growth and propagation of cells outside of a multicellular organism or tissue. Suitable culture conditions for mammalian cells are known in the art. See e.g. Animal cell culture: A Practical Approach, D. Rickwood, ed., Oxford University Press, New York (1992). Mammalian cells may be cultured in suspension or while attached to a solid substrate. Fluidized bed bioreactors, hollow fiber bioreactors, roller bottles, shake flasks, or stirred tank bioreactors, with or without microcarriers, can be used.

The mammalian cell culture is grown in a bioreactor. In one embodiment 500 L to 20000 L bioreactors are used. In a preferred embodiment, 1000 L to 2000 L bioreactors are used.

The bioreactor is inoculated with at least $0.5 \times 10^6$ up to and beyond $3.0 \times 10^6$ viable cells/mL in a serum-free culture medium. In a preferred embodiment the inoculation is $1.0 \times 10^6$ viable cells/mL.

Once inoculated into the production bioreactor the mammalian cells undergo an exponential growth phase. The growth phase can be maintained using a fed-batch process with bolus feeds of a serum-free feed medium having from 5 to 8 g/L glucose. These supplemental bolus feeds typically begin shortly after the cells are inoculated into the bioreactor, at a time when it is anticipated or determined that the cell culture needs feeding. For example, supplemental feeds can begin on or about day 3 or 4 of the culture or a day or two earlier or later. The culture may receive two, three, or more bolus feeds during the growth phase. Neither the basal cell culture medium nor the bolus feed medium contain galactose or sucrose.

When the cells enter the stationary or production phase, or the cell culture has achieved a desired viable cell density and/or cell titer, the fed batch bolus feeds are discontinued and perfusion is started. Perfusion culture is one in which the cell culture receives fresh perfusion feed medium while simultaneously removing spent medium. Perfusion can be continuous, step-wise, intermittent, or a combination of any or all of any of these. Perfusion rates can be less than a working volume to many working volumes per day. Preferably the cells are retained in the culture and the spent medium that is removed is substantially free of cells or has significantly fewer cells than the culture. Perfusion can be accomplished by a number of means including centrifugation, sedimentation, or filtration, See e.g. Voisard et al., (2003), Biotechnology and Bioengineering 82:751-65. A preferred filtration method is alternating tangential flow filtration. Alternating tangential flow is maintained by pumping medium through hollow-fiber filter modules. See e.g. U.S. Pat. No. 6,544,424. The hollow-fiber modules can be microfilters or ultrafilters.

When the fed-batch culture reaches a predetermined trigger point, such as desired cell viability, cell density, percent packed cell volume, titer, packed cell volume adjusted titer, age or the like, a switch between fed-batch and perfusion can take place. For example, this switch can take place on or about day 7 of the culture, but may take place a day or two earlier or later. The perfusion feed formulation contains glucose at a concentration of up to 15 g/L or more, but does not contain galactose or sucrose. In one embodiment, the perfusion medium contains 15 g/L glucose.

When the perfusion culture reaches a predetermined trigger point, such as desired cell viability, cell density, percent packed cell volume, titer, packed cell volume adjusted titer, age or the like, the glucose concentration in the cell culture medium is lowered. For example, this shift may be initiated on day 11 of the culture, but may take place a day or two earlier or later. At that time the cell culture is perfused with cell culture medium containing a lower concentration of glucose. Such a lower concentration of glucose will result in a lower concentration of glucose measured in the spent media of at or nearly 0 g/L. Glucose can be feed at up to 8 g/L. In one embodiment, glucose is fed up to 6 g/L. In another embodiment glucose is fed up to 4 g/L. In another embodiment, glucose is fed up to 3 g/L. In another embodiment glucose is 2-3 g/L. In yet another embodiment, glucose is 2.5 g/L. In another embodiment, glucose is 0 g/L.

The limited glucose state in the cell culture is maintained by monitoring the concentration of glucose in the cell culture, such as by measuring glucose concentration in the spent medium, and adjusting the glucose concentration in the perfusion medium formulation to maintain a level of at or nearly 0 g/L in the spent medium.

The cell culture medium containing the lower concentration of glucose may also be supplemented with galactose at a concentration of up to 20 g/L. In one embodiment the concentration of galactose is from 10 to 15 g/L. In another embodiment the concentration of galactose is 11.5 g/L.

Alternatively, the lower glucose cell culture medium may be supplemented with sucrose at a concentration of 1 to 48 g/L. In one embodiment the sucrose concentration is 16 to 24 g/L.

The cell culture can be continuously maintained in a limited glucose state supplemented with galactose or sucrose. The cell culture can be maintained in a limited glucose state supplemented with galactose or sucrose until harvest. The cell culture can be restored to a non-glucose limited state without galactose or sucrose supplements and the entire process begun again.

The cell culture could also be maintained in a perfusion culture system for both the growth and production phases. Once inoculated into the production bioreactor the mammalian cells undergo an exponential growth phase during which time the cell culture is perfused with serum-free and/or chemically defined cell culture medium supplemented with 5 to 15 g/L glucose. The cell culture medium does not contain galactose or sucrose. The culture is maintained until a desired trigger point is achieved, for example desired viable cell density, cell viability, percent packed cell volume, titer, packed cell adjusted volume titer, age or the like. At that time the cell culture is perfused with a cell culture medium containing a limiting concentration of glucose. Such a limiting concentration of glucose will result in a concentration of glucose in the spent media of at or nearly 0 g/L glucose. Glucose can be feed at up to 8 g/L. In one embodiment, glucose is fed up to 6 g/L. In another embodiment glucose is fed up to 4 g/L. In another embodiment, glucose is fed up to 3 g/L. In another embodiment glucose is 2-3 g/L. In yet another embodiment, glucose is 2.5 g/L. In another embodiment, glucose is 0 g/L.

The cell culture medium containing the limiting amount of glucose may also contain galactose at a concentration of up to 20 g/L. In one embodiment the concentration of galactose is from 10 to 15 g/L. In another embodiment the concentration of galactose is 11.5 g/L.

Alternatively, the cell culture medium containing the limiting amount of glucose may contain sucrose at a concentration from 1 to 48 g/L. One embodiment of the sucrose concentration is 16 to 24 g/L.

In addition, the cell culture medium containing the limiting amount of glucose may also contain glutamine in addition to galactose or sucrose. Glutamine is at a concentration of 1 to 20 mM in combination with either galactose or sucrose. In one embodiment the concentration of glutamine is from 5 to 10 mM.

Viable cell density may be a signal for transition to the production phase or to lower the glucose concentration in the cell culture medium. It may also be desirable to maintain a certain range or level of viable cell density during the production phase. In one embodiment the viable cell density is $10\times10^6$ viable cells/mL to at least about $60\times10^6$ viable cells/mL. In another embodiment the viable cell density is $10\times10^6$ viable cells/mL to $50\times10^6$ viable cells/mL. In another embodiment the viable cell density is $10\times10^6$ viable cells/mL to $40\times10^6$ viable cells/mL. In a preferred embodiment the viable cell density is $10\times10^6$ viable cells/mL to $30\times10^6$ viable cells/mL. In another preferred embodiment the viable cell density is $10\times10^6$ viable cells/mL to $20\times10^6$ viable cells/mL. In another preferred embodiment the viable cell density is $20\times10^6$ viable cells/mL to $30\times10^6$ viable cells/mL. In yet another preferred embodiment the viable cell density is $20\times10^6$ viable cells/mL to $25\times10^6$ viable cells/mL. In an even more preferred embodiment the viable cell density is at least about $20\times10^6$ viable cells/mL.

The percent packed cell volume (% PCV) may also be used as a signal for transition to the production phase or to begin feeding the cell culture with a cell culture medium containing a limiting amount of glucose. The cell culture may also be maintained at a desired packed cell volume during the production phase. In one embodiment the packed cell volume is equal to or less than 30%. In a preferred embodiment the packed cell volume is at least about 15-30%. In a preferred embodiment the packed cell volume is at least about 20-25%. In another preferred embodiment the packed cell volume is equal to or less than 25%. In another preferred embodiment the packed cell volume is equal to or less than 15%. In another preferred embodiment the packed cell volume is equal to or less than 20%. In yet another preferred embodiment the packed cell volume is equal to or less than 15%.

A perfusion cell culture medium having a reduced concentration of asparagine can be used to arrest cell growth while maintaining productivity and viability during the production phase. In a preferred embodiment the concentration of asparagine is at least about 0 mM to at least about 5 mM asparagine, see WIPO Publication No. WO 2013/006479.

As used herein, "perfusion flow rate" is the amount of media that is passed through (added and removed) from a bioreactor, typically expressed as some portion or multiple of the working volume, in a given time. "Working volume" refers to the amount of bioreactor volume used for cell culture. In one embodiment the perfusion flow rate is one working volume or less per day. Perfusion feed medium can be formulated to maximize perfusion nutrient concentration to minimize perfusion rate.

As used herein, "cell density" refers to the number of cells in a given volume of culture medium. "Viable cell density" refers to the number of live cells in a given volume of culture medium, as determined by standard viability assays (such as trypan blue dye exclusion method).

As used herein, "packed cell volume" (PCV), also referred to as "percent packed cell volume" (% PCV), is the ratio of the volume occupied by the cells, to the total volume of cell culture, expressed as a percentage (see Stettler, wt al., (2006) Biotechnol Bioeng. December 20:95(6):1228-33). Packed cell volume is a function of cell density and cell diameter; increases in packed cell volume could arise from increases in either cell density or cell diameter or both. Packed cell volume is a measure of the solid content in the cell culture. Solids are removed during harvest and downstream purification. More solids mean more effort to separate the solid material from the desired product during harvest and downstream purification steps. Also, the desired product can become trapped in the solids and lost during the harvest process, resulting in a decreased product yield. Since host cells vary in size and cell cultures also contain dead and dying cells and other cellular debris, packed cell volume is a more accurate way to describe the solid content within a cell culture than cell density or viable cell density.

For the purposes of this invention, cell culture medium is a medium suitable for growth of animal cells, such as mammalian cells, in in vitro cell culture. Cell culture media formulations are well known in the art. Typically, cell culture media are comprised of buffers, salts, carbohydrates, amino acids, vitamins and trace essential elements. "Serum-free" applies to a cell culture medium that does not contain animal sera, such as fetal bovine serum. Various tissue culture media, including defined culture media, are commercially available, for example, any one or a combination of the following cell culture media can be used: RPMI-1640 Medium, RPMI-1641 Medium, Dulbecco's Modified Eagle's Medium (DMEM), Minimum Essential Medium Eagle, F-12K Medium, Ham's F12 Medium, Iscove's Modified Dulbecco's Medium, McCoy's 5A Medium, Leibovitz's L-15 Medium, and serum-free media such as EX-CELL' 300 Series (JRH Biosciences, Lenexa, Kans.), among others. Serum-free versions of such culture media are also available. Cell culture media may be supplemented with additional or increased concentrations of components such as amino acids, salts, sugars, vitamins, hormones, growth factors, buffers, antibiotics, lipids, trace elements and the like, depending on the requirements of the cells to be cultured and/or the desired cell culture parameters.

Cell culture media may be serum-free, protein-free, and/or peptone-free. "Serum-free" applies to a cell culture medium that does not contain animal sera, such as fetal bovine serum. "Protein-free" applies to cell culture media free from exogenously added protein, such as transferrin, protein growth factors IGF-1, or insulin. Protein-free media may or may not contain peptones. "Peptone-free" applies to cell culture media which contains no exogenous protein hydrolysates such as animal and/or plant protein hydrolysates. Cell culture broth or like terminology refers to the cell culture media that contains, among other things, viable and non-viable mammalian cells, cell metabolites and cellular debris such as nucleic acids, proteins and liposomes.

Cell cultures can also be supplemented with concentrated feed medium containing components, such as nutrients and amino acids, which are consumed during the course of the production phase of the cell culture. Concentrated feed medium may be based on just about any cell culture media formulation. Such a concentrated feed medium can contain anywhere from a single or nearly almost all of the components of the cell culture medium at, for example, about 5×, 6×, 7×, 8×, 9×, 10×, 12×, 14×, 16×, 20×, 30×, 50×, 100×, 200×, 400×, 600×, 800×, or even about 1000× of their normal amount, see for example WIPO Publication No WO2012/145682.

The method according to the present invention may be used to improve the production of recombinant proteins in multiple phase culture processes. In a multiple stage process, cells are cultured in two or more distinct phases. For example cells may be cultured first in one or more growth phases, under environmental conditions that maximize cell proliferation and viability, then transferred to a production phase, under conditions that maximize protein production. In a commercial process for production of a protein by mammalian cells, there are commonly multiple, for example, at least about 2, 3, 4, 5, 6, 7, 8, 9, or 10 growth phases that occur in different culture vessels preceding a final production culture. The growth and production phases may be preceded by, or separated by, one or more transition phases. In multiple phase processes, the method according to the present invention can be employed at least during the growth and production phase of the final production phase of a commercial cell culture, although it may also be employed in a preceding growth phase. A production phase can be conducted at large scale. A large scale process can be conducted in a volume of at least about 100, 500, 1000, 2000, 3000, 5000, 7000, 8000, 10,000, 15,000, 20,000 liters. In a preferred embodiment production is conducted in 500 L, 1000 L and/or 2000 L bioreactors. A growth phase may occur at a higher temperature than a production phase. For example, a growth phase may occur at a first temperature from about 35° C. to about 38° C., and a production phase may occur at a second temperature from about 29° C. to about 37° C., optionally from about 30° C. to about 36° C. or from about 30° C. to about 34° C. In addition, chemical inducers of protein production, such as, for example, caffeine, butyrate, and hexamethylene bisacetamide (HMBA), may be added at the same time as, before, and/or after a temperature shift. If inducers are added after a temperature shift, they can be added from one hour to five days after the temperature shift, optionally from one to two days after the temperature shift. The cell cultures can be maintained for days or even weeks while the cells produce the desired protein(s).

Typically the cell cultures that precede the final production culture (N-x to N-1) are used to generate the seed cells that will be used to inoculate the production bioreactor, the N-1 culture. The seed cell density can have a positive impact on the level of recombinant protein produced. Product levels tend to increase with increasing seed density. Improvement in titer is tied not only to higher seed density, but is likely to be influenced by the metabolic and cell cycle state of the cells that are placed into production.

Seed cells can be produced by any culture method. A preferred method is a perfusion culture using alternating tangential flow filtration. An N-1 bioreactor can be run using alternating tangential flow filtration to provide cells at high density to inoculate a production bioreactor. The N-1 stage may be used to grow cells to densities of $>90\times10^6$ cells/mL. The N-1 bioreactor can be used to generate bolus seed cultures or can be used as a rolling seed stock culture that could be maintained to seed multiple production bioreactors at high seed cell density. The duration of the growth stage of production can range from 7 to 14 days and can be designed so as to maintain cells in exponential growth prior to inoculation of the production bioreactor. Perfusion rates, medium formulation and timing are optimized to grow cells and deliver them to the production bioreactor in a state that is most conducive to optimizing their production. Seed cell densities of $>15\times10^6$ cells/mL can be achieved for seeding production bioreactors.

The cell lines (also referred to as "host cells") used in the invention are genetically engineered to express a polypeptide of commercial or scientific interest. Cell lines are typically derived from a lineage arising from a primary culture that can be maintained in culture for an unlimited time. Genetically engineering the cell line involves transfecting, transforming or transducing the cells with a recombinant polynucleotide molecule, and/or otherwise altering (e.g., by homologous recombination and gene activation or fusion of a recombinant cell with a non-recombinant cell) so as to cause the host cell to express a desired recombinant polypeptide. Methods and vectors for genetically engineering cells and/or cell lines to express a polypeptide of interest are well known to those of skill in the art; for example, various techniques are illustrated in *Current Protocols in Molecular Biology*, Ausubel et al., eds. (Wiley & Sons, New York, 1988, and quarterly updates); Sambrook et al., Molecular Cloning: A Laboratory Manual (Cold Spring Laboratory Press, 1989); Kaufman, R. J., *Large Scale Mammalian Cell Culture*, 1990, pp. 15-69.

Animal cell lines are derived from cells whose progenitors were derived from a multi-cellular animal. One type of animal cell line is a mammalian cell line. A wide variety of mammalian cell lines suitable for growth in culture are available from the American Type Culture Collection (Manassas, Va.) and commercial vendors. Examples of cell lines commonly used in the industry include VERO, BHK, HeLa, CV1 (including Cos), MDCK, 293, 3T3, myeloma cell lines (e.g., NSO, NS1), PC12, W138 cells, and Chinese hamster ovary (CHO) cells. CHO cells are widely used for the production of complex recombinant proteins, e.g. cytokines, clotting factors, and antibodies (Brasel et al. (1996), *Blood* 88:2004-2012; Kaufman et al. (1988), *J. Biol Chem* 263: 6352-6362; McKinnon et al. (1991), *J. Mol Endocrinol* 6:231-239; Wood et al. (1990), *J. Immunol.* 145:3011-3016). The dihydrofolate reductase (DHFR)-deficient mutant cell lines (Urlaub et al. (1980), *Proc Natl Acad Sci USA* 77: 4216-4220), DXB11 and DG-44, are desirable CHO host cell lines because the efficient DHFR selectable and amplifiable gene expression system allows high level recombinant protein expression in these cells (Kaufman R. J. (1990), *Meth Enzymol* 185:537-566). In addition, these cells are easy to manipulate as adherent or suspension cultures and exhibit relatively good genetic stability. CHO cells and proteins recombinantly expressed in them have been extensively characterized and have been approved for use in clinical commercial manufacturing by regulatory agencies.

The methods of the invention can be used to culture cells that express recombinant proteins of interest. The expressed recombinant proteins may be secreted into the culture medium from which they can be recovered and/or collected. In addition, the proteins can be purified, or partially purified, from such culture or component (e.g., from culture medium) using known processes and products available from commercial vendors. The purified proteins can then be "formulated", meaning buffer exchanged, sterilized, bulk-packaged, and/or packaged for a final user. Suitable formulations for pharmaceutical compositions include those described in *Remington's Pharmaceutical Sciences*, 18th ed. 1995, Mack Publishing Company, Easton, Pa.

As used herein "peptide," "polypeptide" and "protein" are used interchangeably throughout and refer to a molecule comprising two or more amino acid residues joined to each other by peptide bonds. Peptides, polypeptides and proteins are also inclusive of modifications including, but not limited to, glycosylation, lipid attachment, sulfation, gamma-carboxylation of glutamic acid residues, hydroxylation and ADP-ribosylation. "Glycoprotein" refers to peptides, polypeptides and proteins, having at least one oligosaccharide side chain including mannose residues. Glycoproteins may be homologous to the host cell, or may be heterologous, i.e., foreign, to the host cell being utilized, such as, for example, a human glycoprotein produced by a Chinese hamster ovary (CHO) host-cell. Polypeptides can be of scientific or commercial interest, including protein-based drugs. Polypeptides include, among other things, antibodies, fusion proteins, and cytokines. Peptides, polypeptides and proteins are produced by recombinant animal cell lines using cell culture methods and may be referred to as "recombinant peptide", "recombinant polypeptide" and "recombinant protein". The expressed protein(s) may be produced intracellularly or secreted into the culture medium from which it can be recovered and/or collected.

Examples of polypeptides that can be produced with the methods of the invention include proteins comprising amino acid sequences identical to or substantially similar to all or part of one of the following proteins: tumor necrosis factor (TNF), flt3 ligand (WO 94/28391), erythropoeitin, thrombopoeitin, calcitonin, IL-2, angiopoietin-2 (Maisonpierre et al. (1997), *Science* 277(5322): 55-60), ligand for receptor activator of NF-kappa B (RANKL, WO 01/36637), tumor necrosis factor (TNF)-related apoptosis-inducing ligand (TRAIL, WO 97/01633), thymic stroma-derived lymphopoietin, granulocyte colony stimulating factor, granulocyte-macrophage colony stimulating factor (GM-CSF, Australian Patent No. 588819), mast cell growth factor, stem cell growth factor (U.S. Pat. No. 6,204,363), epidermal growth factor, keratinocyte growth factor, megakaryote growth and development factor, RANTES, human fibrinogen-like 2 protein (FGL2; NCBI accession no. NM 00682; Rüegg and Pytela (1995), Gene 160:257-62) growth hormone, insulin, insulinotropin, insulin-like growth factors, parathyroid hormone, interferons including α-interferons, γ-interferon, and consensus interferons (U.S. Pat. Nos. 4,695,623 and 4,897, 471), nerve growth factor, brain-derived neurotrophic factor, synaptotagmin-like proteins (SLP 1-5), neurotrophin-3, glucagon, interleukins, colony stimulating factors, lymphotoxin-β, leukemia inhibitory factor, and oncostatin-M. Descriptions of other glycoproteins may be found in, for example, *Human Cytokines: Handbook for Basic and Clinical Research*, all volumes (Aggarwal and Gutterman, eds. Blackwell Sciences, Cambridge, Mass., 1998); *Growth Factors: A Practical Approach* (McKay and Leigh, eds., Oxford University Press Inc., New York, 1993); and *The Cytokine Handbook*, Vols. 1 and 2 (Thompson and Lotze eds., Academic Press, San Diego, Calif., 2003).

Additionally the methods of the invention would be useful to produce proteins comprising all or part of the amino acid sequence of a receptor for any of the above-mentioned proteins, an antagonist to such a receptor or any of the above-mentioned proteins, and/or proteins substantially similar to such receptors or antagonists. These receptors and antagonists include: both forms of tumor necrosis factor receptor (TNFR, referred to as p55 and p'75, U.S. Pat. Nos. 5,395,760 and 5,610,279), Interleukin-1 (IL-1) receptors (types I and II; EP Patent No. 0460846, U.S. Pat. Nos. 4,968,607, and 5,767,064), IL-1 receptor antagonists (U.S. Pat. No. 6,337,072), IL-1 antagonists or inhibitors (U.S. Pat. Nos. 5,981,713, 6,096,728, and 5,075,222) IL-2 receptors, IL-4 receptors (EP Patent No. 0 367 566 and U.S. Pat. No. 5,856,296), IL-15 receptors, IL-17 receptors, IL-18 receptors, Fc receptors, granulocyte-macrophage colony stimulating factor receptor, granulocyte colony stimulating factor receptor, receptors for oncostatin-M and leukemia inhibitory factor, receptor activator of NF-kappa B (RANK, WO 01/36637 and U.S. Pat. No. 6,271,349), osteoprotegerin (U.S. Pat. No. 6,015,938), receptors for TRAIL (including TRAIL receptors 1, 2, 3, and 4), and receptors that comprise death domains, such as Fas or Apoptosis-Inducing Receptor (AIR).

Other proteins that can be produced using the invention include proteins comprising all or part of the amino acid sequences of differentiation antigens (referred to as CD proteins) or their ligands or proteins substantially similar to either of these. Such antigens are disclosed in *Leukocyte Typing VI* (*Proceedings of the VIth International Workshop and Conference*, Kishimoto, Kikutani et al., eds., Kobe, Japan, 1996). Similar CD proteins are disclosed in subsequent workshops. Examples of such antigens include CD22, CD27, CD30, CD39, CD40, and ligands thereto (CD27 ligand, CD30 ligand, etc.). Several of the CD antigens are members of the TNF receptor family, which also includes 41BB and OX40. The ligands are often members of the TNF family, as are 41BB ligand and OX40 ligand.

Enzymatically active proteins or their ligands can also be produced by the invention. Examples include proteins comprising all or part of one of the following proteins or their ligands or a protein substantially similar to one of these: a disintegrin and metalloproteinase domain family members including TNF-alpha Converting Enzyme, various kinases, glucocerebrosidase, superoxide dismutase, tissue plasminogen activator, Factor VIII, Factor IX, apolipoprotein E, apolipoprotein A-I, globins, an IL-2 antagonist, alpha-1 antitrypsin, ligands for any of the above-mentioned enzymes, and numerous other enzymes and their ligands.

The term "antibody" includes reference to immunoglobulins of any isotype or subclass or to an antigen-binding region thereof that competes with the intact antibody for specific binding, unless otherwise specified, including human, humanized, chimeric, multi-specific, monoclonal, polyclonal, and oligomers or antigen binding fragments thereof. Also included are proteins having an antigen binding fragment or region such as Fab, Fab', F(ab')2, Fv, diabodies, Fd, dAb, maxibodies, single chain antibody molecules, complementarity determining region (CDR) fragments, scFv, diabodies, triabodies, tetrabodies and polypeptides that contain at least a portion of an immunoglobulin that is sufficient to confer specific antigen binding to a target polypeptide. The term "antibody" is inclusive of, but not limited to, those that are prepared, expressed, created or isolated by recombinant means, such as antibodies isolated from a host cell transfected to express the antibody.

Examples of antibodies include, but are not limited to, those that recognize any one or a combination of proteins including, but not limited to, the above-mentioned proteins and/or the following antigens: CD2, CD3, CD4, CD8, CD11a, CD14, CD18, CD20, CD22, CD23, CD25, CD33, CD40, CD44, CD52, CD80 (B7.1), CD86 (B7.2), CD147, IL-1α, IL-1β, IL-2, IL-3, IL-7, IL-4, IL-5, IL-8, IL-10, IL-2 receptor, IL-4 receptor, IL-6 receptor, IL-13 receptor, IL-18 receptor subunits, FGL2, PDGF-β and analogs thereof (see U.S. Pat. Nos. 5,272,064 and 5,149,792), VEGF, TGF, TGF-β2, TGF-β1, EGF receptor (see U.S. Pat. No. 6,235, 883) VEGF receptor, hepatocyte growth factor, osteoprotegerin ligand, interferon gamma, B lymphocyte stimulator (BlyS, also known as BAFF, THANK, TALL-1, and zTNF4; see Do and Chen-Kiang (2002), *Cytokine Growth Factor Rev.* 13(1): 19-25), C5 complement, IgE, tumor antigen CA125, tumor antigen MUC1, PEM antigen, LCG (which is a gene product that is expressed in association with lung cancer), HER-2, HER-3, a tumor-associated glycoprotein TAG-72, the SK-1 antigen, tumor-associated epitopes that are present in elevated levels in the sera of patients with colon and/or pancreatic cancer, cancer-associated epitopes or proteins expressed on breast, colon, squamous cell, prostate, pancreatic, lung, and/or kidney cancer cells and/or on melanoma, glioma, or neuroblastoma cells, the necrotic core of a tumor, integrin alpha 4 beta 7, the integrin VLA-4, B2 integrins, TRAIL receptors 1, 2, 3, and 4, RANK, RANK ligand, TNF-α, the adhesion molecule VAP-1, epithelial cell adhesion molecule (EpCAM), intercellular adhesion molecule-3 (ICAM-3), leukointegrin adhesin, the platelet glycoprotein gp IIb/IIIa, cardiac myosin heavy chain, parathyroid hormone, rNAPc2 (which is an inhibitor of factor VIIa-tissue factor), MHC I, carcinoembryonic antigen (CEA), alpha-fetoprotein (AFP), tumor necrosis factor (TNF), CTLA-4 (which is a cytotoxic T lymphocyte-associated antigen), Fc-γ-1 receptor, HLA-DR 10 beta, HLA-DR antigen, sclerostin, L-selectin, Respiratory Syncitial Virus, human immunodeficiency virus (HIV), hepatitis B virus (HBV), *Streptococcus mutans*, and *Staphlycoccus aureus*. Specific examples of known antibodies which can be produced using the methods of the invention include but are not limited to adalimumab, bevacizumab, infliximab, abciximab, alemtuzumab, bapineuzumab, basiliximab, belimumab, briakinumab, canakinumab, certolizumab pegol, cetuximab, conatumumab, denosumab, eculizumab, gemtuzumab ozogamicin, golimumab, ibritumomab tiuxetan, labetuzumab, mapatumumab, matuzumab, mepolizumab, motavizumab, muromonab-CD3, natalizumab, nimotuzumab, ofatumumab, omalizumab, oregovomab, palivizumab, panitumumab, pemtumomab, pertuzumab, ranibizumab, rituximab, rovelizumab, tocilizumab, tositumomab, trastuzumab, ustekinumab, vedolizumab, zalutumumab, and zanolimumab.

The invention can be used to produce recombinant fusion proteins comprising, for example, any of the above-mentioned proteins. For example, recombinant fusion proteins comprising one of the above-mentioned proteins plus a multimerization domain, such as a leucine zipper, a coiled coil, an Fc portion of an immunoglobulin, or a substantially similar protein, can be produced using the methods of the invention. See e.g. WO94/10308; Lovejoy et al. (1993), *Science* 259:1288-1293; Harbury et al. (1993), *Science* 262:1401-05; Harbury et al. (1994), *Nature* 371:80-83; Hakansson et al. (1999), *Structure* 7:255-64. Specifically included among such recombinant fusion proteins are proteins in which a portion of a receptor is fused to an Fc portion of an antibody such as etanercept (a p75 TNFR:Fc), and belatacept (CTLA4:Fc). In another embodiment are antibody-drug conjugates.

While the terminology used in this application is standard within the art, definitions of certain terms are provided herein to assure clarity and definiteness to the meaning of the claims. Units, prefixes, and symbols may be denoted in their SI accepted form. Numeric ranges recited herein are inclusive of the numbers defining the range and include and are supportive of each integer within the defined range. Unless otherwise noted, the terms "a" or "an" are to be construed as meaning "at least one of". The section headings used herein are for organizational purposes only and are not to be construed as limiting the subject matter described. The methods and techniques described herein are generally performed according to conventional methods well known in the art and as described in various general and more specific references that are cited and discussed throughout the present specification unless otherwise indicated. See, e.g., Sambrook et al. Molecular Cloning: A Laboratory Manual, 3rd ed., Cold Spring Harbor Laboratory Press, Cold Spring Harbor, N.Y. (2001) and Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990). All documents, or portions of documents, cited in this application, including but not limited to patents, patent applications, articles, books, and treatises, are hereby expressly incorporated by reference.

The present invention is not to be limited in scope by the specific embodiments described herein that are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

The following examples demonstrate embodiments and aspects of the disclosed methods and are not intended to be limiting.

EXAMPLES

The substitution of alternative carbohydrate species for glucose within a bioreactor system for the purposes of manipulating high mannose glycoform content and overall protein quality is addressed.

Example 1

Fed-Batch Culture with Continuous Glucose Feed and Bolus Galactose Feed

The effects of reduced glucose and an alternative carbon source on cell culture growth, titer and product quality, particularly the Man5 levels, was evaluated by testing different glucose and galactose concentrations using a fed-batch process. The goal of the experimental was to reduce the amount of glucose available in the cell culture medium, while providing a different carbon source through a galactose feed.

Twelve 2 L Applikon bioreactors were inoculated with CHO cells expressing a recombinant IgG2 antibody at 20e5 viable cells/mL in a working volume of 1 L of a serum free cell culture medium. Cultures were maintained at 36° C., 30% dissolved oxygen (DO), 290 rpm agitation, and pH of 6.95. A tyrosine-cystine supplement was fed on days 2 and 5, volumetrically at 0.36% based on the initial volume. CO2 and 1M sodium carbonate base were added as needed for pH control.

Bolus feeding of culture media was on days 2, 5 at 9, volumetrically based on 9% of the initial volume.

A two-factor experiment design was chosen to evaluate cell culture performance and product quality attributes with varying amounts of glucose and galactose in the cell culture medium. The experiment design consisted of 6 treatments, duplicate bioreactors for each treatment as shown in Table 1. The first factor was continuous glucose feeding (continuous glucose) to deliver 3, 2, or 1 g/day of glucose starting from day 2. The treatments with 3 g/day glucose also received additional bolus glucose feeds to maintain the glucose concentration at 3 g/L. The purpose was to ensure that 3 g/day treatments were maintained as positive controls, never having a glucose limitation.

The second factor was bolus feeds with (1+, 2+, 3+) and without (1-, 2-, 3-) galactose (bolus galactose). The objective was to maintain the concentration of galactose in the cell culture media above 4 g/L starting on day 2.

TABLE 1

The 2-factor experimental design for the fed-batch experiment

| Run | Continuous Glucose, g/day | Bolus Galactose, g/L |
|---|---|---|
| 719 | 2 | 0 |
| 720 | 3 + bolus glu | 0 |

TABLE 1-continued

The 2-factor experimental design for the fed-batch experiment

| Run | Continuous Glucose, g/day | Bolus Galactose, g/L |
|---|---|---|
| 721 | 3 + bolus glu | 4 |
| 722 | 1 | 0 |
| 723 | 1 | 4 |
| 724 | 2 | 0 |
| 725 | 2 | 4 |
| 726 | 3 + bolus glu | 0 |
| 727 | 2 | 4 |
| 728 | 1 | 0 |
| 729 | 3 + bolus glu | 4 |
| 730 | 1 | 4 |

During the culture run, daily samples were taken to assess the culture. Viable cell density (VCD) and viability were determined bench scale using Vi-Cell (Beckman Coulter, Brea, Calif.). Packed cell volume was determined using VoluPAC (Sartorius, Goettingen, Germany). pH, dissolved carbon dioxide (pCO2), and dissolved oxygen (p02) were determined using a Siemens 248 blood gas analyzer (BGA) (Chiron Diagnostics, CA. Galactose concentration was obtained using a YSI Model 2700 Select Biochemistry Analyzer (YSI Incorporated, Yellow Springs, Ohio). Metabolite data (glucose, lactate, and ammonia) was obtained using Polymedco Polychem Analyzer (Polymedco Inc., Cortland Manor, N.Y.). Osmolality was determined using an Advanced Instruments model 2020 micro osmometer (Advanced Instruments, Norwood, Mass.). Supernatant samples were stored at −80° C. At the end of experiments, frozen cell-free supernatant samples were thawed and collectively submitted for titer and glycan analysis.

Titer was determined using HPLC analysis. Cell culture supernatant samples from different time points were thawed and re-filtered in a 96 well plate with 0.2 μm membrane. The samples were injected to a HPLC system (Hewlett Packard 1100) equipped with UV detection at 280 nm using Poros® A/20 2.1 mm D×30 mm L column (Applied Biosystems, Foster City, Calif.) at a flow rate of 2 mL/min. Gradient method using mobile phase 100 mM sodium phosphate/250 mM sodium chlorite and 2% Acetic acid/100 mM glycine were used to elute each protein sample for every 5 min.

For glycan analysis, cell culture supernatant samples were collected and purified by Protein A. The purified samples were treated with PNGase-F and incubated at 37° C. for 2 hours to release the N-linked glycans. The enzymatically released glycans were labeled with 2-aminobenzoic acid (2-AA) at 80° C. for 75 minutes. Excess 2-AA label was then removed with a Glycoclean S cartridge. The samples were evaporated overnight and the resulting dry pellet was reconstituted with water for subsequent HILIC (hydrophilic interaction liquid chromatography) analysis. The glycans were injected and bound to the column in high organic conditions and eluted with an increasing gradient of an aqueous ammonium formate buffer. Fluorescence detection was used to monitor the glycan elution and the relative percentage of the major and minor glycan species were calculated.

Results from Fed-Batch Process with Continuous Glucose Feed and Bolus Galactose Feed The cell culture treatments that received 3 g/day of continuous glucose feed (Runs 720, 721, 726, and 729), also received bolus glucose feed to keep their level above 3 g/L. Runs 720 and 726, which received no bolus galactose feed, routinely required bolus feeds of glucose, while the runs receiving galactose (runs 721 and 729) did not require bolus glucose feeds as often. The cell cultures receiving 1 or 2 g/day of continuous glucose feed, did not receive any additional bolus glucose feeds. The spent media analysis of these cultures showed the glucose concentration was 0 g/L on day 4 regardless of whether or not the culture received bolus galactose feeds. (FIG. 1A).

Figure 1B:
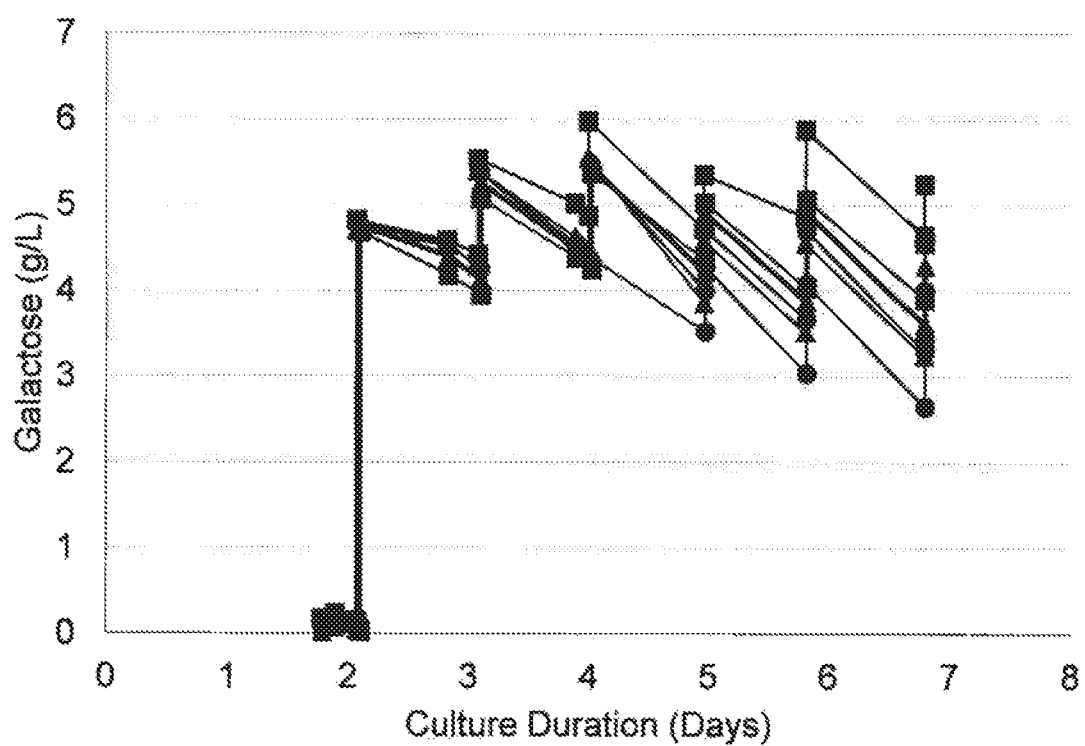

The cell cultures receiving bolus galactose feeds (Runs 721, 723, 725, 727, 729, and 730), maintained galactose levels above 2.5 g/L although the original target was above 4 g/L. (FIG. 1B) When the galactose consumption numbers were analyzed, it was found that there was a statistically significant difference in how much galactose the cultures consumed for the cultures with limited glucose (Runs receiving 2 g/day or 1 g/day continuous glucose feed) or without limited glucose (Runs receiving 3 g/day continuous glucose feed plus bolus glucose feed). The cultures with limited glucose consumed an average of 4.60 grams of galactose total, while those without a limitation on glucose consumed an average of 3.81 grams.

Figure 1C:
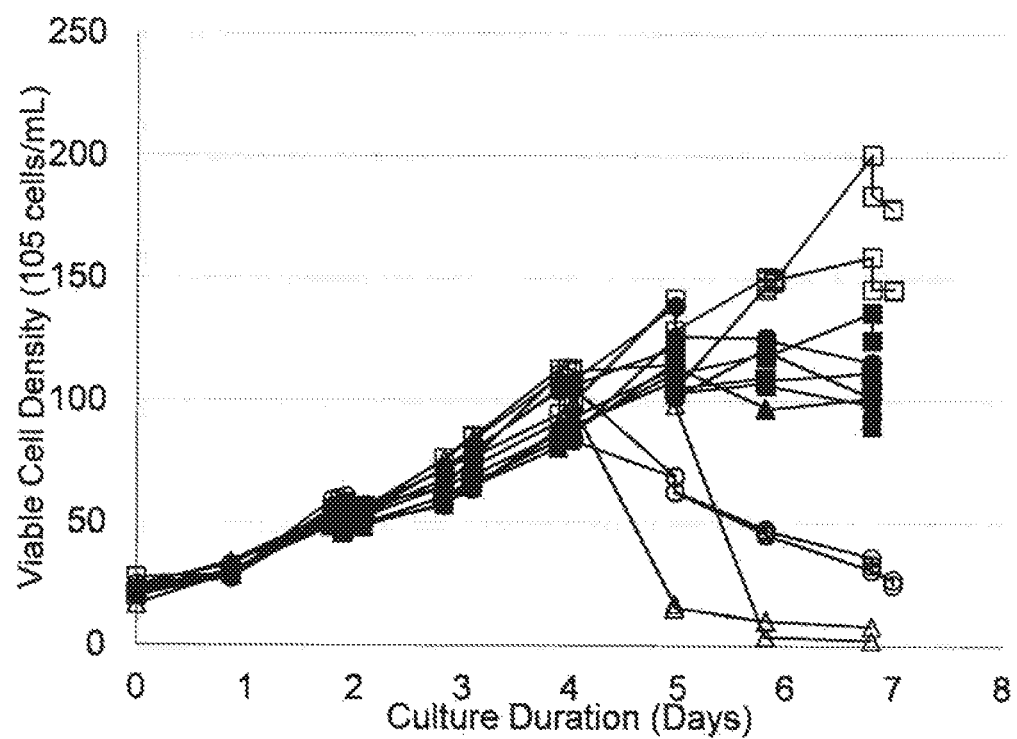
Figure 1D:
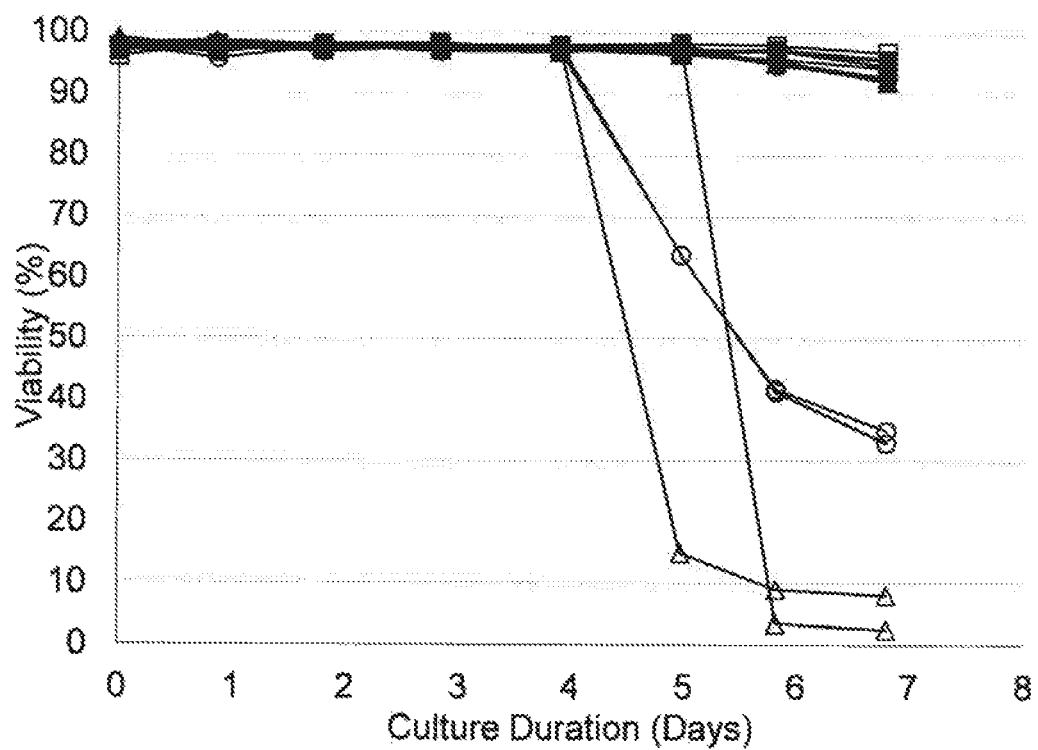

The continuous glucose feeds and bolus galactose feeds had significant impact on viable cell density and viability. The cultures with limited glucose (Runs receiving 2 g/day or 1 g/day continuous glucose feed), along with a bolus galactose feed, maintained good viable cell density and viability. However, the cultures with limited glucose (Runs receiving 2 g/day or 1 g/day continuous glucose feed) that did not receive bolus galactose feeds could not maintain viable cell density and viability once the glucose reached a limitation on day 4. (FIGS. 1C and 1D)

Figure 1E:
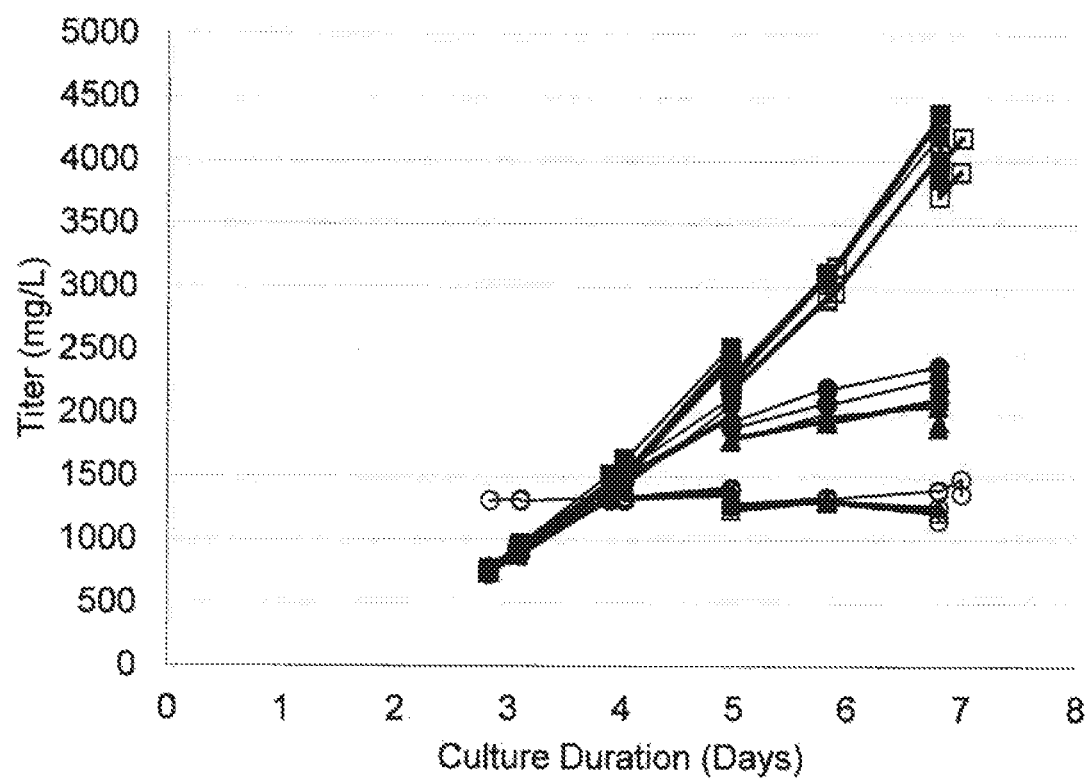

The above data indicated that galactose could be used as an alternative carbon source when glucose was limited in the cell culture medium. Although the cultures with limited glucose (Runs receiving 2 g/day or 1 g/day continuous glucose feed), along with bolus galactose feed, maintained good viable cell density and viability, the titer was reduced significantly compared to those cultures with no glucose limitation (Runs receiving 3 g/day continuous glucose feed), see FIG. 1E. Statistical analysis showed that the continuous glucose feed level had the greatest effect on titer; the bolus galactose feed was also significant, but to a lesser degree.

Figure 1F:
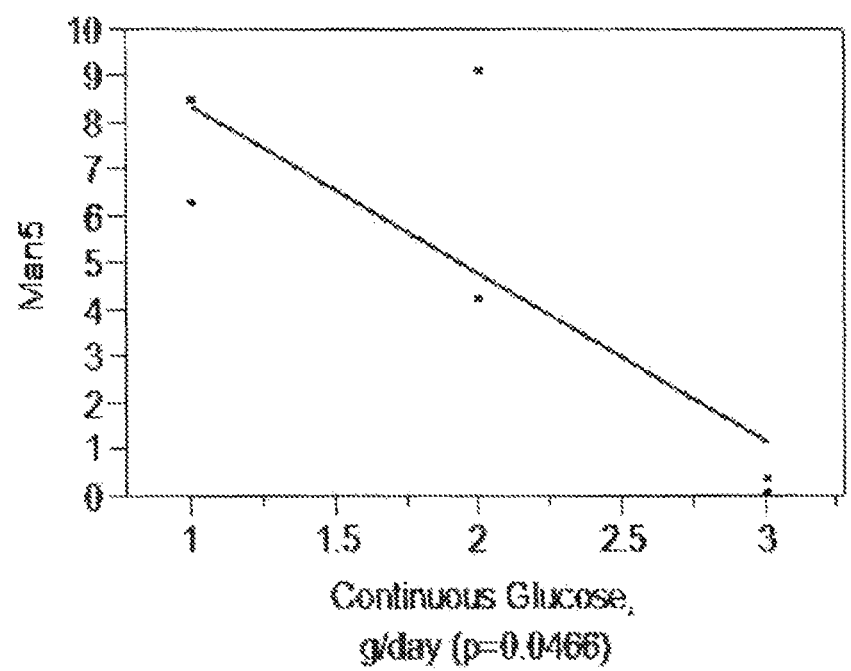

The Man5 levels in the day 7 samples were reduced in proportion to the increase of glucose feed from 1 g/day to 3 g/day regardless of whether there was a galactose feed. Limited glucose was the only statistically significant factor that resulted in Man5 increase in culture. (FIG. 1F)

Example 2

Perfusion Process with Limited Glucose, Galactose as Alternative Carbon Source and the Addition of Glutamine The above fed-batch study showed that limiting glucose was the only factor that resulted in Man5 increase; however cultures with limited glucose could not maintain viable cell density or cell viability. The alternative carbon source, galactose, did not result in Man5 increase, but was catabolized by the CHO cells and maintained good viable cell density and cell viability in those cultures where it was added. However, titer was reduced significantly with limited glucose levels even with alternative carbon source present. Achieving desirable product quality without significant improvement in titer is not commercially viable, which is the same case as achieving significant improvement in titer without comparable product quality.

In order to achieve the goals of maintaining or improving titer and achieving desirable product quality, the effects of low glucose and an alternative carbon source on cell culture performance and Man5 levels were tested in a perfusion cell culture. The experiment design consisted of 3 treatments, duplicate bioreactors for each treatment.

On day 0, CHO cells expressing a recombinant IgG2 antibody were inoculated into 3 L production bioreactors at $1\times10^6$ viable cells/mL in a working volume of 1300 ml of a serum-free defined cell culture medium containing 5-8 g/L glucose. Cultures were maintained at 36° C., dissolved oxygen at 30%, agitation at 400 RPM. The culture was grown in batch mode for three days. The concentration of glucose in spent medium analysis ranged from 1-8 g/L.

On days 3 and 6 the culture received bolus feeds of a concentrated serum-free defined feed media, 8% initial working volume on day 3 and 8% initial working volume on day 6. Bolus glucose feeds were done on days 3, 4, 5, 6, 7 to maintain a target concentration of 8 g/L glucose in the culture. Glucose in spent medium analysis ranged from 1-8 g/L.

Perfusion was started on day 7 at a perfusion rate of 0.48 Vol/day. Perfusion was accomplished using an alternating tangential flow perfusion and filtration system (Refine Technologies, Hanover, N.J.) with a 30 kDa hollow fiber filter (GE Healthcare, Uppsala, Sweden). The serum free defined perfusion medium, pH 7.0, contained 15 g/L glucose. Glucose in spent medium analysis ranged from 3-8 g/L.

On day 11 the switch was made to a serum free, defined perfusion medium now containing galactose and having a reduced amount of glucose, see Table 2a. The concentration of glucose in the perfusion medium was decreased to 2 g/L or 4 g/L. Galactose was compounded into the medium at 6 g/L. Bolus feeds of a 30% galactose stock solution were used as needed to maintain galactose at a concentration of 4 g/L or above in the cell culture.

For this experiment, the perfusion culture medium also included glutamine at 5 or 10 mM to determine if glutamine, like glucose, had any effect on viable cell density, cell viability, titer and/or Man5 levels in a situation of glutamine limitation. The literature suggested that low glutamine concentrations could have a negative impact on cell culture. The cultures were perfused with this cell culture medium until harvest on day 17.

Figure 2A:
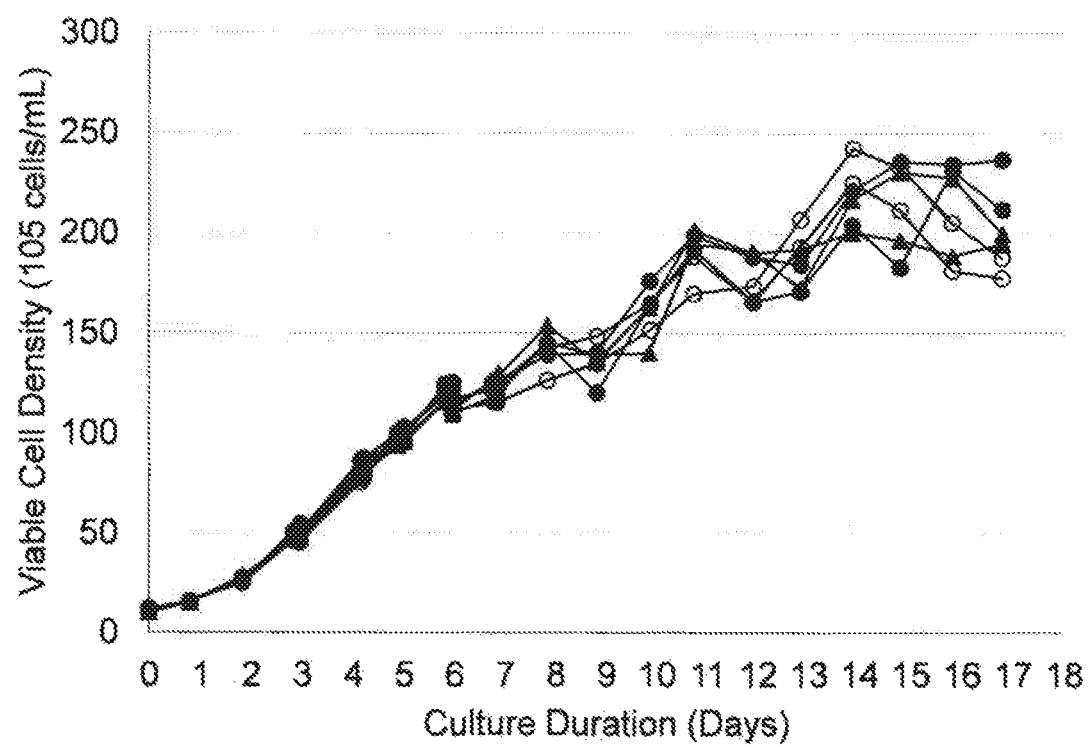
FIG. 2. Cell culture and amino acid profiles in perfusion process. (A) Viable Cell Density (B) Viability, (C) Gln (glutamine) concentration g/L in spent media analysis, (D) Packed Cell Volume Adjusted Titer, (E) Glc (glucose) concentration g/L in spent media analysis, (F) galactose concentration g/L in spent media analysis. Glucose 2 g/L, galactose 6 g/L and glutamine 10 mM (solid triangle). Glucose 4 g/L, galactose 6 g/L and glutamine 10 mM (solid circle). Glucose 4 g/L, galactose 6 g/L and glutamine 5 mM (open circle).
Figure 2B:
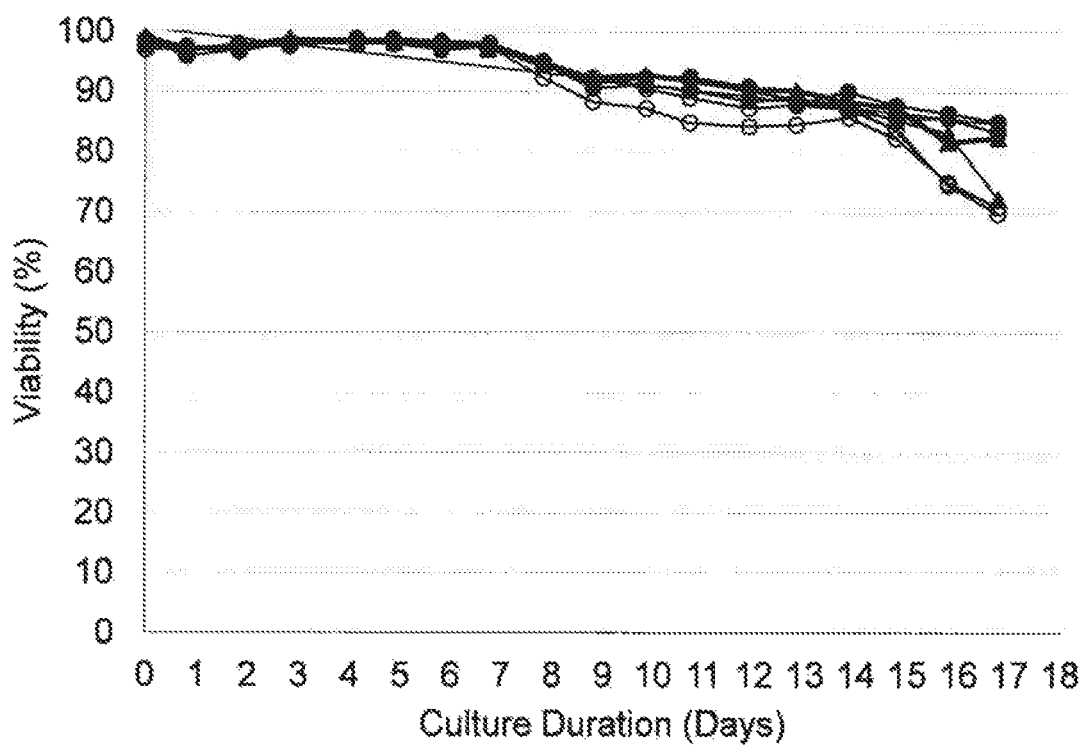
Figure 2C:
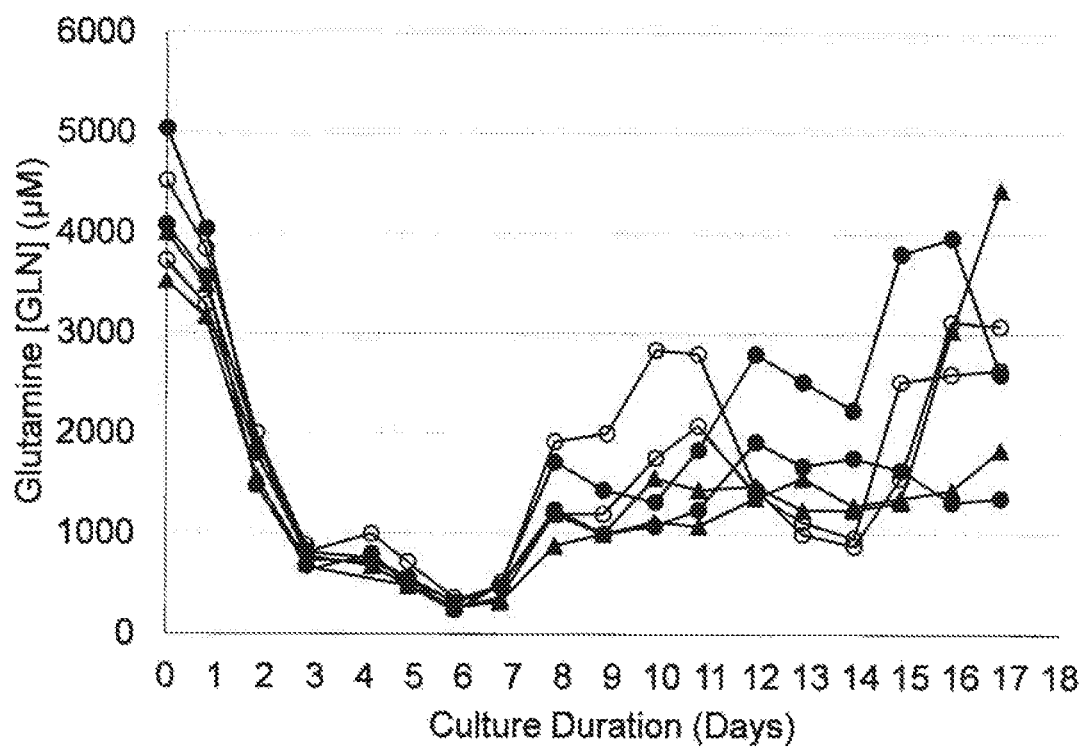
Figure 2D:
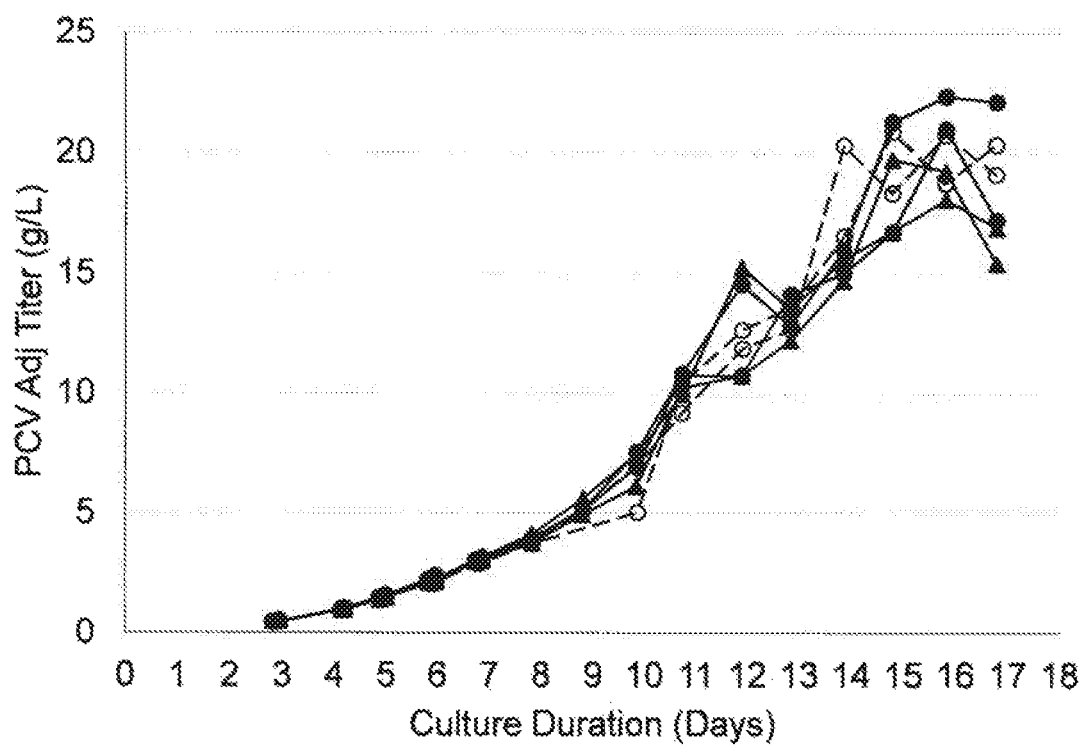

The surprising finding was that the packed cell volume adjusted Titer (PCV Titer) shown in FIG. 2D was close to the values seen for a perfusion process that was not glucose limited. The titer from the perfusion experiments in this example was much greater that that seen in the fed-batch process of Example 1 which only yielded a 50% titer. These data indicate that the cells exhibit a different physiological state when glucose limited in a perfusion process than they do in a fed batch process.

Figure 2E:
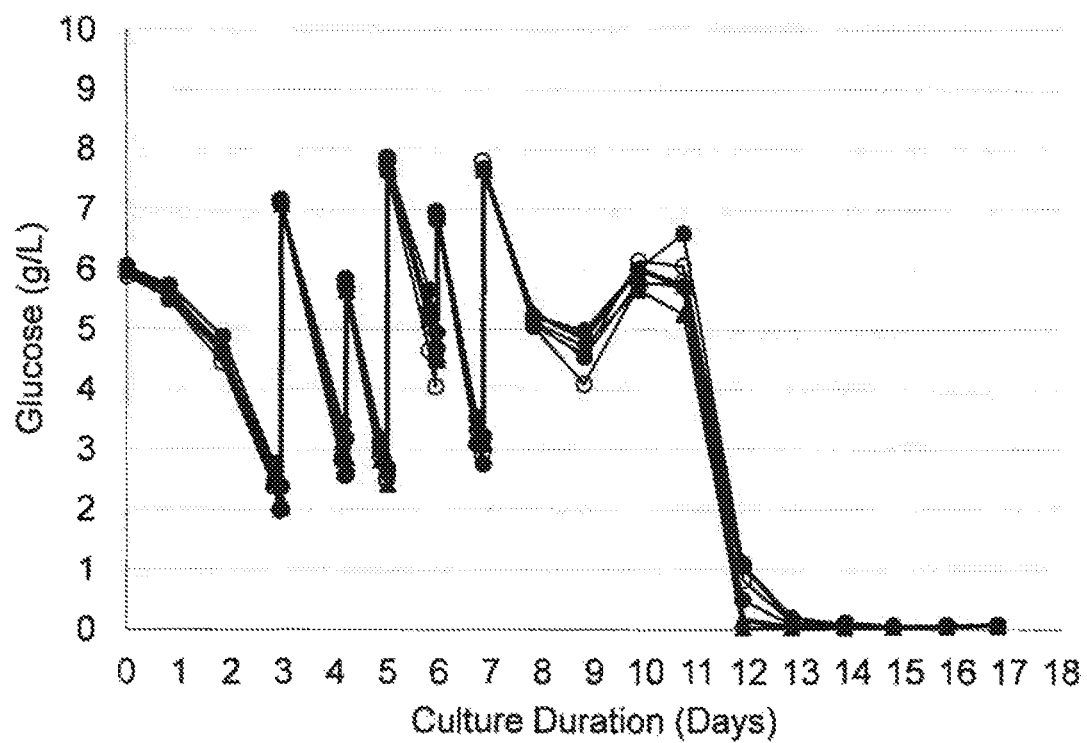

Spent media analysis show that the glucose concentration in culture supernatants treated with 2 g/L glucose in the perfusion medium reached zero on day 12 and the glucose concentration in culture supernatants treated with 4 g/L glucose reached zero on day 13, except for Run 83 (FIG. 2E). The spend media analysis confirmed that the cultures were in a limited glucose state.

Figure 2F:
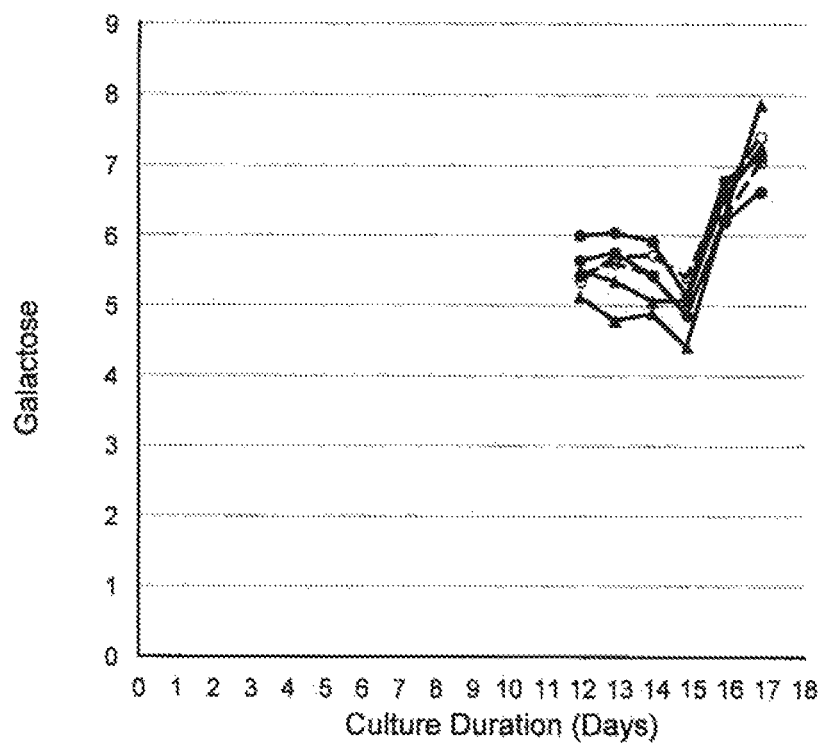
Figure 3A:
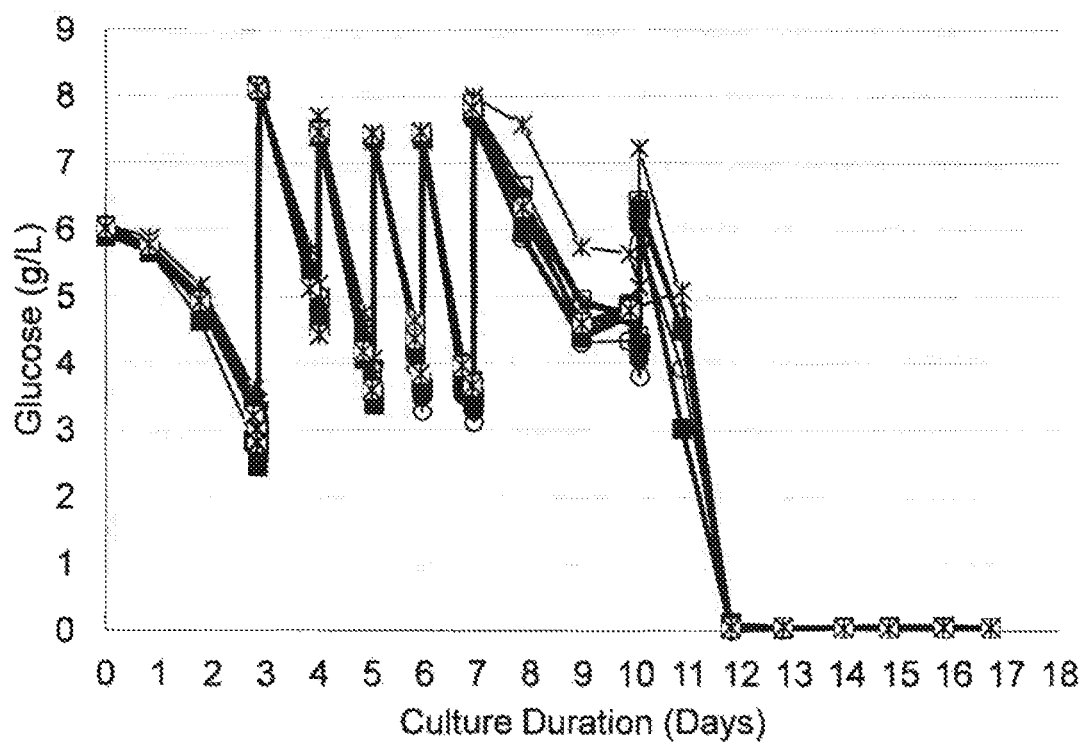
FIG. 3. Cell culture profiles in perfusion process. (A) Glu (glucose) concentration g/L in spent media analysis, (B) Gal (galactose) concentration g/L in spent media analysis, (C) Lactate concentration, (D) Ammonia concentration (E) Viable cell density, (F) Viability, (G) Packed cell volume adjusted titer. Glucose 3 g/L, galactose 13 g/L (solid square). Glucose 0 g/L, galactose 10 g/L (open circle). Glucose 0 g/L, galactose 13 g/L (solid circle). Glucose 1.5 g/L, galactose 11.5 g/L (star). Glucose 3 g/L, galactose 10 g/L, (open square).
Figure 3B:
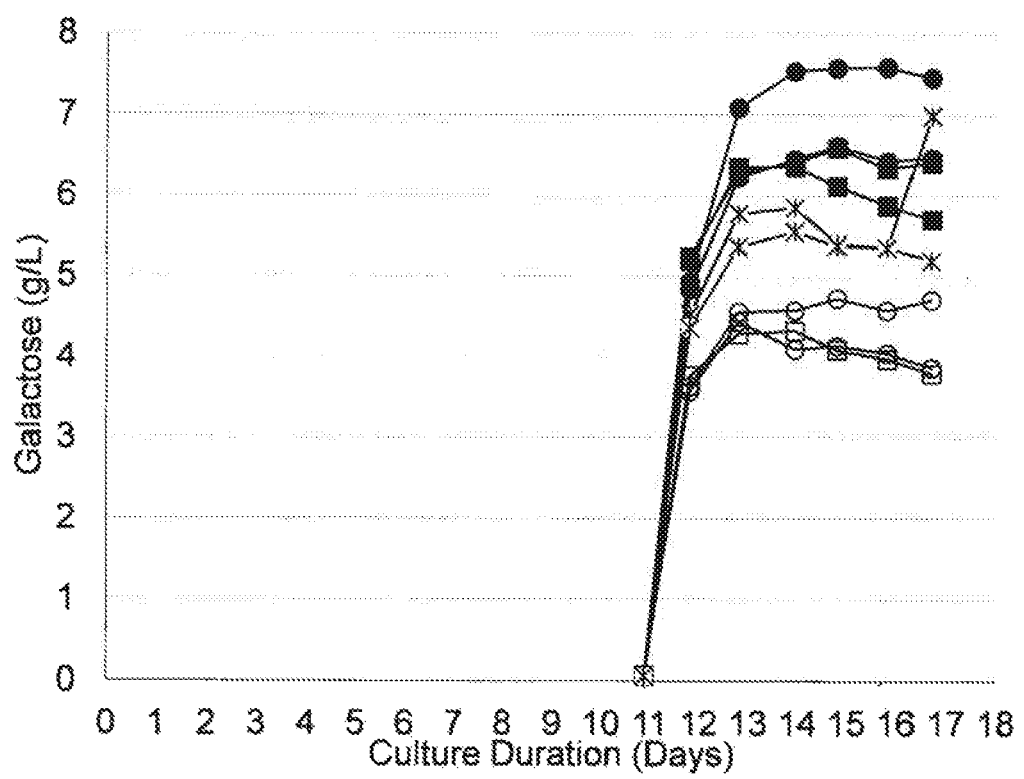
Figure 3C:
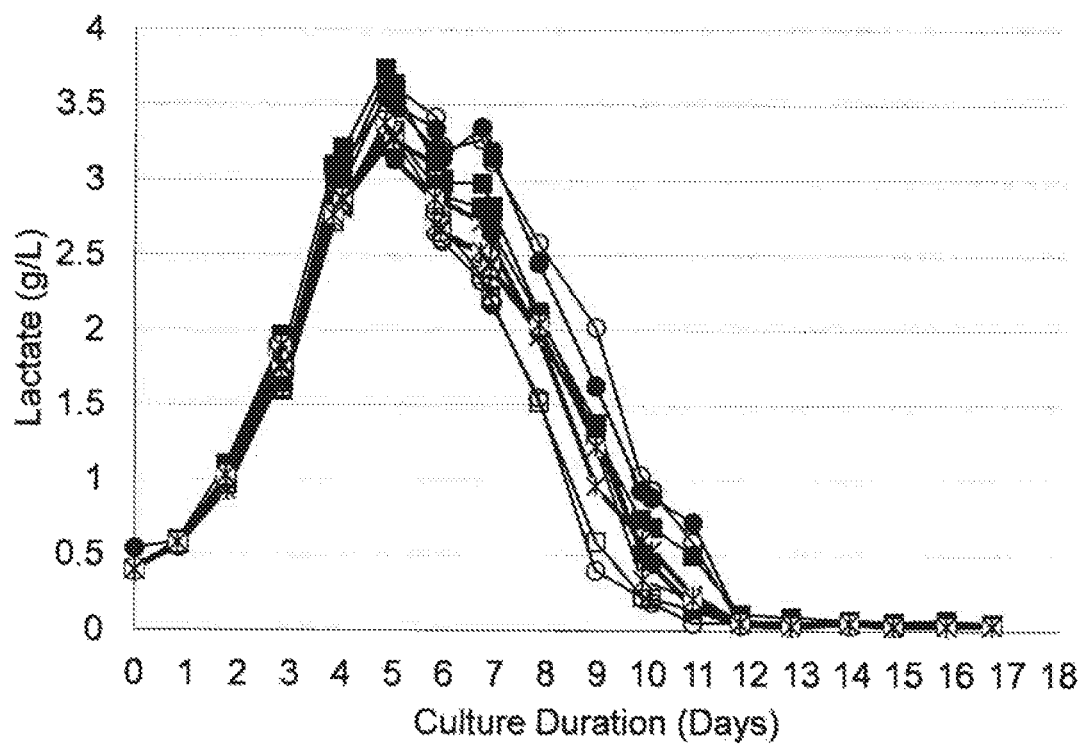
Figure 3D:
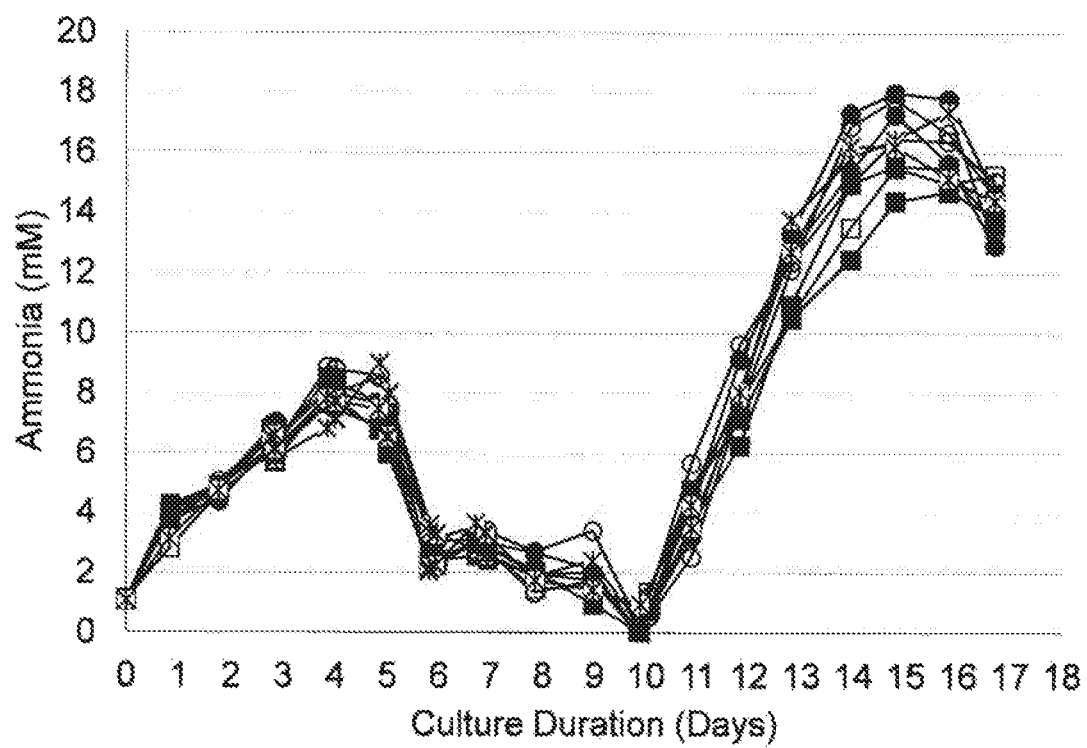
Figure 3E:
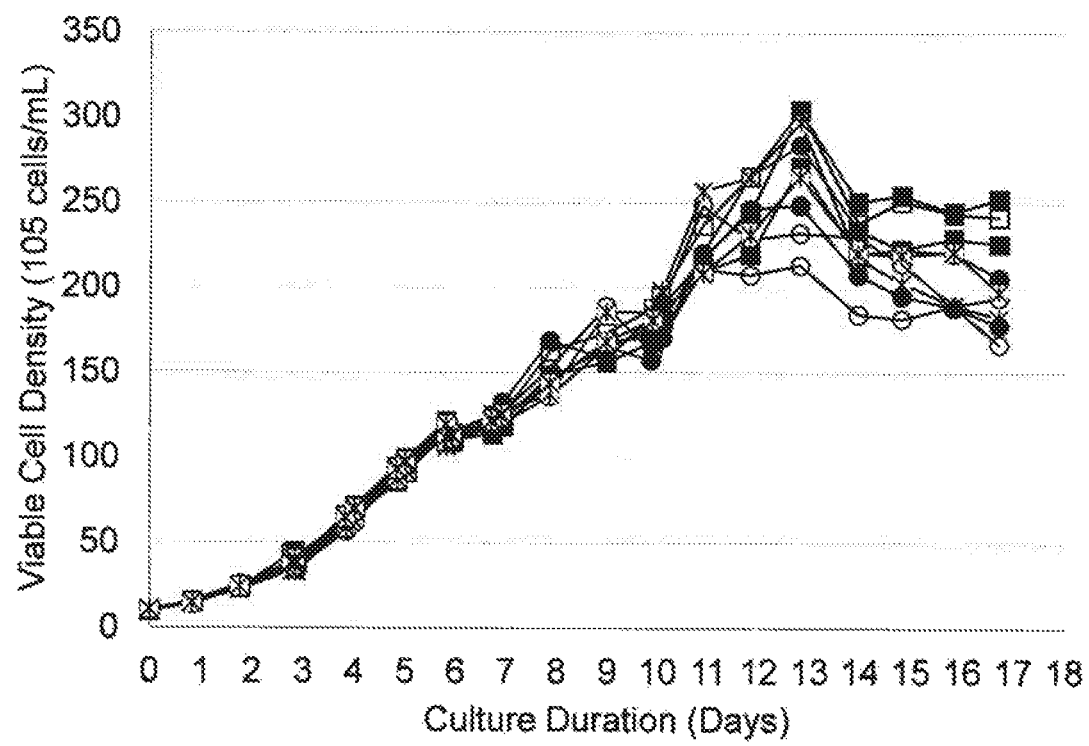
Figure 3F:
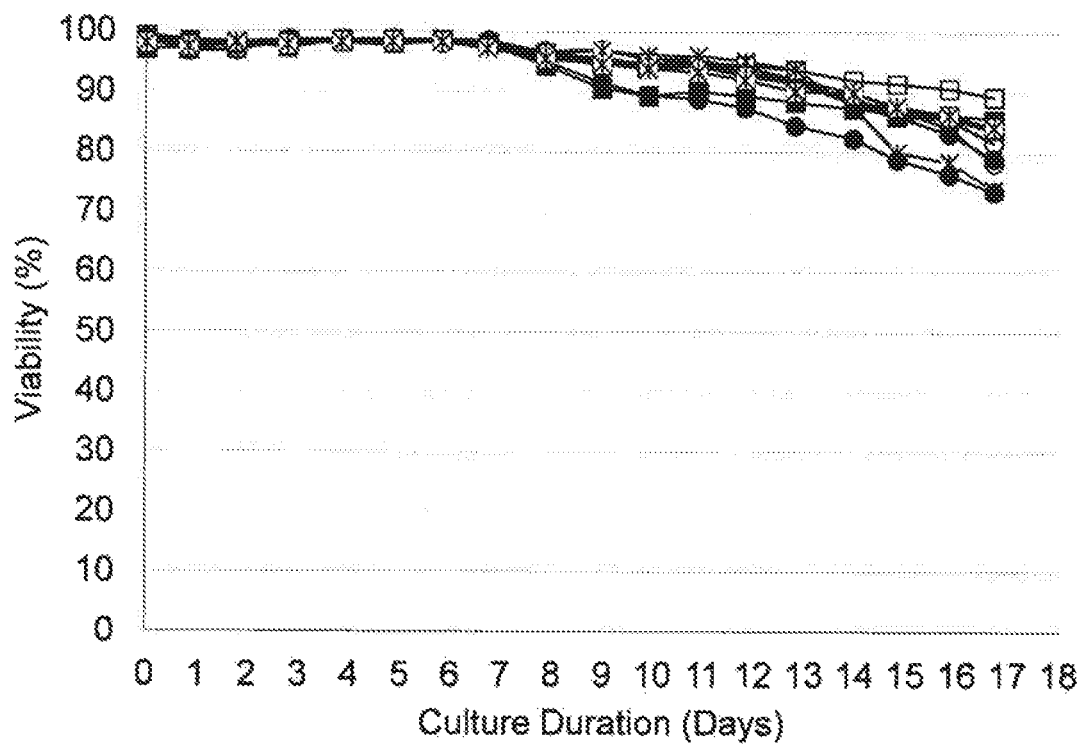
Figure 3G:
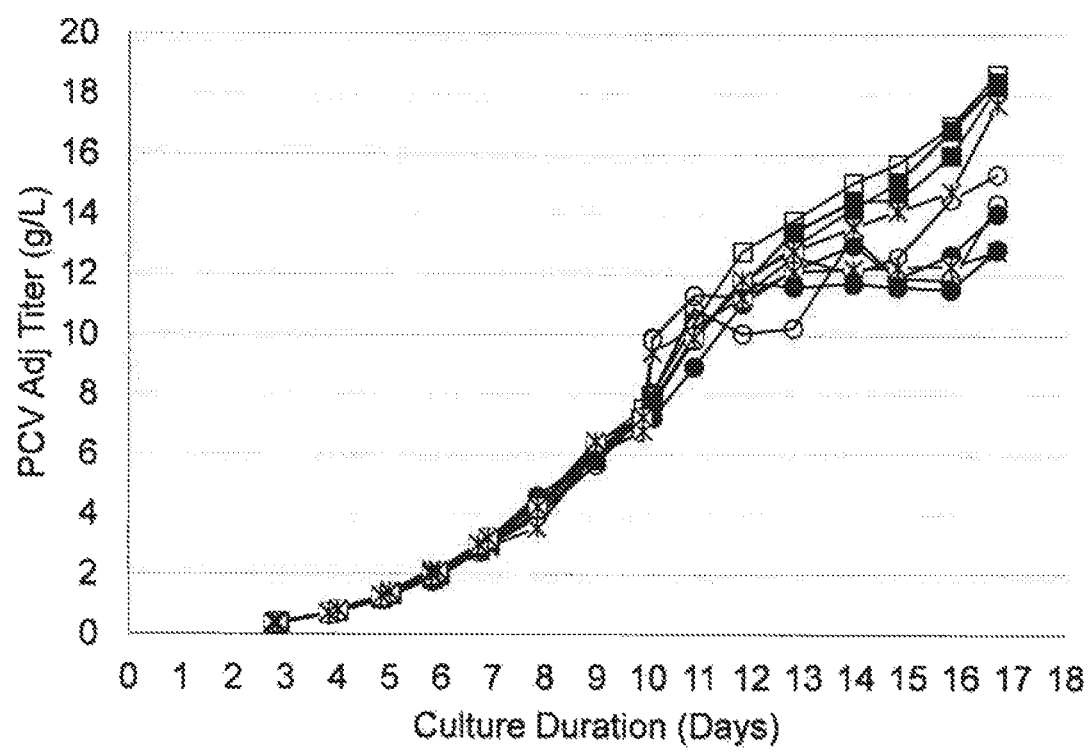

In general, the concentration of galactose in culture determined by spent media analysis remained above 4 g/L (FIG. 2F).

Table 2b shows that Man5 species increased when the glucose concentration in the perfusion medium was lowered to 2 g/L. The time course data shows that the Man5 species increased with an increase in culture duration (Day 15 to Day 17). All things being equal, when the concentration of glucose in the perfusion medium was increased to 4 g/L, the Man5 species decreased accordingly. These results indicate that limiting glucose resulted in an increase in Man5 levels and that the limited state could be initiated by reducing glucose concentration in the perfusion cell culture medium to 2 g/L or lower and confirming with spent media analysis. However, process variation and cell mass can impact glucose limitation and the modification in Man5 species. Run 83, showed a higher Man5 value than any other run receiving glucose at 4 g/L. In this case Run 83 had a higher viable cell density and packed cell volume adjusted titer (FIGS. 2A and 2D) than any of the cultures receiving 2 g/L glucose (Runs 79 and 81) but like Runs 79 and 81, it reached a lower glucose concentration as measured by spent medium analysis on day 12. This was earlier than any culture receiving glucose at 4 g/L (FIG. 2E). Therefore, factors such as cell mass and/or process variation can impact the glucose feed concentration resulting in a limited glucose situation. In this case where cell density was higher on day 12 (FIG. 2A) leading to a near 0 g/L concentration of glucose in the spent medium, a limited glucose state was initiated even though the cell culture was fed with a high glucose (4 g/L) perfusion feed medium. Once glucose was limited, Man5 levels increased.

TABLE 2a

Concentration of glucose, galactose and glutamine in the day 11 serum free defined perfusion culture medium (pH 7.0)

| Run | Glucose g/L | Galactose g/L | Glutamine mM |
|---|---|---|---|
| 79 | 2 | 6 | 10 |
| 81 | 2 | 6 | 10 |
| 82 | 4 | 6 | 10 |
| 83 | 4 | 6 | 10 |
| 88 | 4 | 6 | 5 |
| 89 | 4 | 6 | 5 |

Cell culture profiles are shown in FIG. 2. The viable cell density and viability profiles show comparable trends (FIGS. 2A and 2B). The viability of the low glucose (2 g/L) and the low glutamine (5 mM) conditions showed a downward trend between day 15 and 17. However, the concentration of glutamine in the spent media analysis indicated that glutamine was not limited under any of the conditions tested (FIG. 2C)

TABLE 2b

Man5% at day 15 and 17 following the change in perfusion medium formulation at day 11

| Run | Glucose g/L | Galactose g/L | Glutamine mM | Day 15 Man5% | Day 17 Man5% |
|---|---|---|---|---|---|
| 79 | 2 | 6 | 10 | 9.29 | 9.84 |
| 81 | 2 | 6 | 10 | 9.28 | 9.49 |
| 82 | 4 | 6 | 10 | 4.64 | 5.62 |
| 83 | 4 | 6 | 10 | 7.56 | 8.91 |
| 88 | 4 | 6 | 5 | 5.19 | 5.65 |
| 89 | 4 | 6 | 5 | 5.09 | 5.63 |

Example 3

Perfusion Process with a Combination of Reduced Glucose and High Galactose

An experiment was performed with a serum free defined perfusion medium (pH 7.0) formulated with glucose at concentrations of 0, 1.5 or 3 g/L. Galactose was added at 10, 11.5 or 13 g/L, based on the total consumption rate of experiment described above. Both glucose and galactose were compounded into perfusion media so the culture could be maintained without bolus feeds of either glucose or galactose. Compounding reduced the complexity of the process and improved consistency. The experiment was performed as described above; using the same feeding strategies on days 0 to 10. Table 3 provides the combinations of perfusion medium formulations used on days 11 through 17.

TABLE 3

Experiment design of glucose and galactose in perfusion media.

| Run | Glucose g/L | Galactose g/L |
|---|---|---|
| 103 | 3 | 13 |
| 104 | 0 | 10 |
| 105 | 0 | 13 |
| 106 | 0 | 10 |
| 107 | 1.5 | 11.5 |
| 108 | 0 | 13 |
| 109* | 3 | 10 |
| 111 | 3 | 13 |
| 112 | 3 | 10 |
| 113 | 1.5 | 11.5 |

*Run 109 was excluded from the figures due to bioreactor operational failure.

The cell culture profiles in FIG. 3 show that all cell culture conditions tested were glucose limited following the day 11 switch (FIG. 3A) and the galactose concentrations measured in the spent medium assay was maintained between 4 to 8 g/L (FIG. 3B) which was proportional to the galactose concentrations compounded in perfusion medium. The lactate level dipped to zero once glucose reached a limitation on day 12 (FIG. 3C). The ammonia level increased starting on day 10, before glucose reached a limitation (FIG. 3D). It was very interesting to see that lowering glucose concentration starting on day 11 resulted in lower growth, viability, and titer (FIGS. 3E-3G). These results indicate that the limited glucose, not glutamine limitation, causes titer reduction in a perfusion process as well as the fed-batch process in Example 1. Also, since glucose levels of 2-3 g/L, and even up to 4 g/L, resulted in the increase in Man5 levels, the glucose levels also provided some help in maintaining higher titer levels.

Figure 4A:
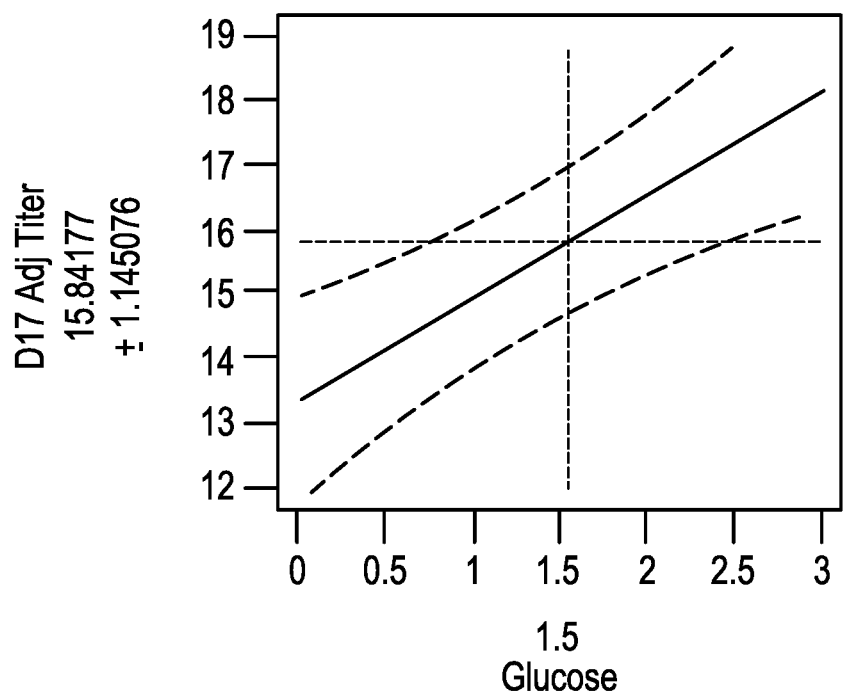
FIG. 4. JMP statistical analysis of perfusion process. (A) Packed Cell Volume Adjusted Titer, (B) Man5.
Figure 4B:
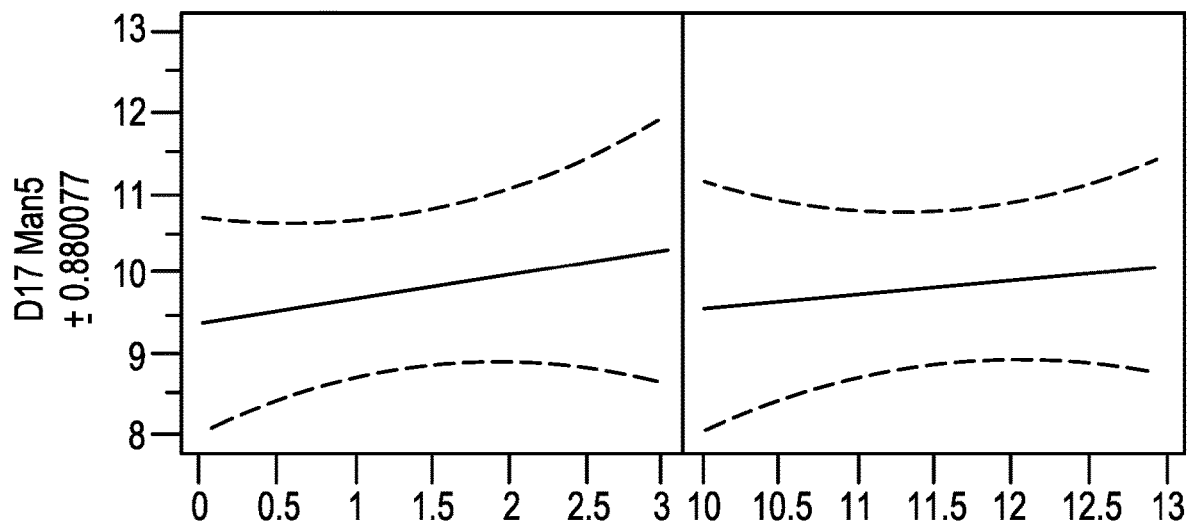

Statistical analysis using JMP software (JMP Inc. Cary, N.C.) revealed that glucose concentration was the only statistically significant (p value=0.032) factor that impacted titer. The galactose was not statistically significant factor for titer (FIG. 4A). On the other hand, both glucose and galactose were not statistically significant factors that impacted Man5 species, but the interaction between glucose and galactose was statistically significant (p value=0.0613). (FIG. 4B). The higher the galactose concentration the greater the effect of the limited glucose on Man5 species.

Figure 5:
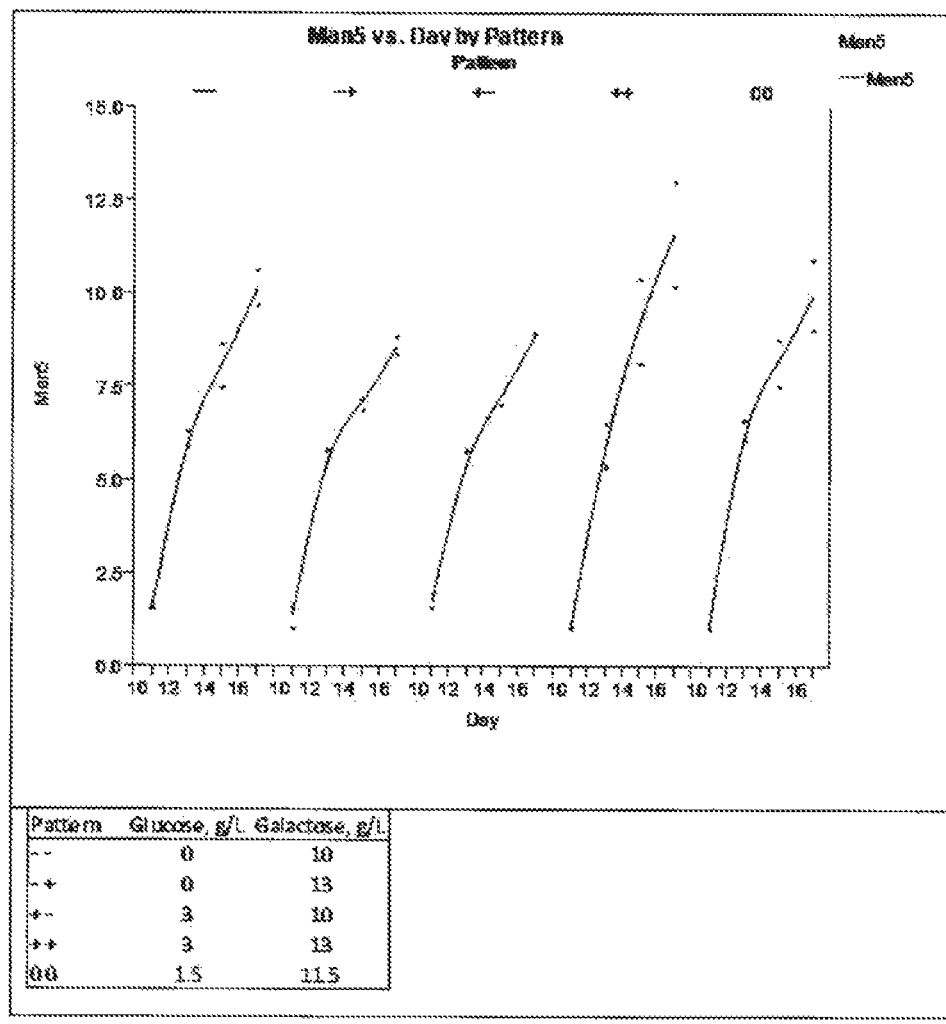
FIG. 5. Time course data showing increase in percent of Man5 species. −0 g/L glucose 10 g/L galactose; −+0 g/L glucose 13 g/L galactose; +13 g/L glucose 10 g/L galactose; ++3 g/L glucose 13 g/L galactose; OO 1.5 g/L glucose 11.5 galactose.

Overall the Man5 levels increased and leveled off when glucose ranged from 0 to 3 g/L and decreased when the glucose levels were 4 g/L or greater. FIG. 5 shows the increase in percent of Man5 species on day 11, 13, 15, and 17. For all culture conditions, percent Man5 species started at about 2% on day 11 and then gradually increased to over 10% on day 17. The most significant increase in percent Man5 species was on days 11 to 13 when glucose became limited.

Since glucose impacts titer, glucose should be fed at the highest concentration that will still support an increase in Man5 while maintaining cell viability, density and titer at an acceptable level, based on the conditions of the cell culture, such as cell mass, the cell culture process and the alternate carbon source used. For example, for a perfusion cell culture having from 15 to 25×10$^6$ cells/ml, glucose concentrations of 0-4 g/L in combination with galactose at 10-13 g/L, resulted in an increase of Man5.

Example 4

Perfusion Process with Limited Glucose and Sucrose as Alternative Carbon Source

Sucrose was identified as another carbon source associated with an increase in Man5 levels. In this experiment, the same culture conditions as described in Example 3 were used, except on day 11, glucose concentrations were 2, 4, and 6 g/L and sucrose was used in place of galactose at concentrations of 16, 20, and 24 g/L. Both glucose and sucrose were compounded into perfusion media without additional bolus feeds of either sugar after day 11, see Table 4.

TABLE 4

Experiment design of glucose and sucrose in perfusion media.

| Run | Glucose g/L | Sucrose g/L |
|---|---|---|
| 153 | 6 | 24 |
| 164 | 2 | 16 |
| 155 | 2 | 24 |
| 156 | 2 | 24 |
| 157 | 4 | 20 |
| 158 | 6 | 16 |
| 159* | 2 | 16 |
| 160 | 6 | 24 |
| 162 | 6 | 16 |
| 163 | 4 | 20 |

*Run 159 was excluded from JMP analysis due to bioreactor operational failure on day 14

Figure 6A:
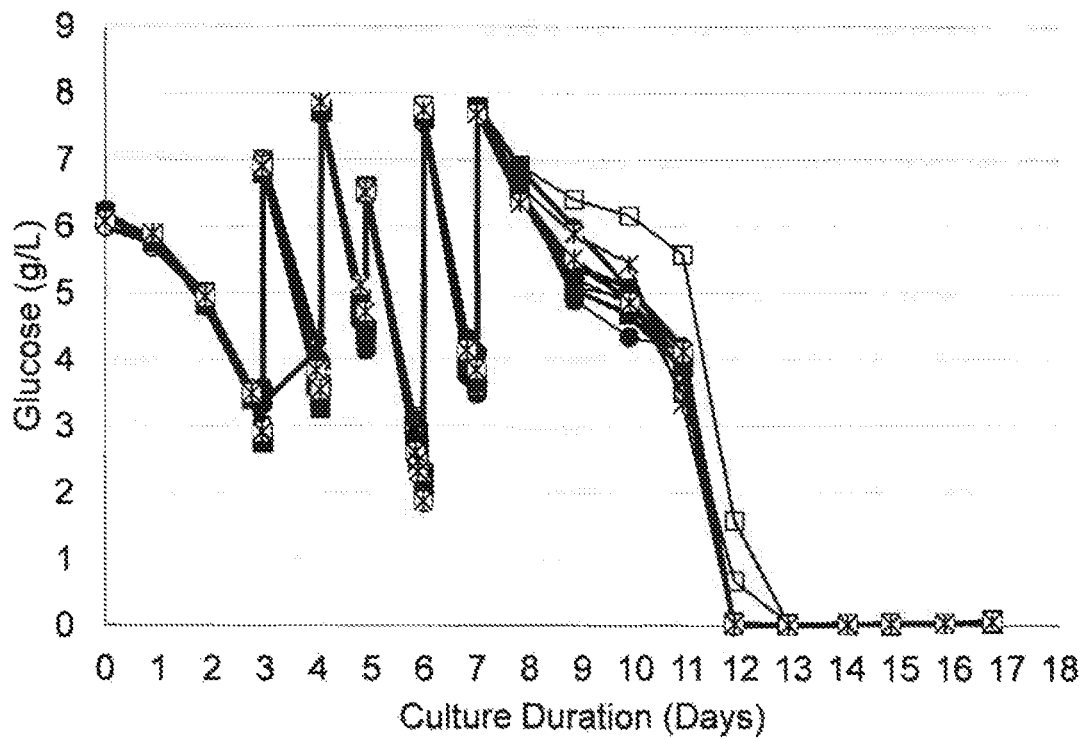
FIG. 6. Cell culture profiles in perfusion process. (A) Glu (glucose) concentration g/L in spent media analysis, (B) Sucrose concentration g/L in spent media analysis, (C) Viable Cell Density, (D) Lactate concentration g/L, (E) Ammonium concentration mM, (F) Viability, (G) Packed Cell Volume Adjusted titer. Glucose 6 g/L, sucrose 24 g/L (solid square). Glucose 2 g/L, sucrose 16 g/L (open square). Glucose 2 g/L, sucrose 24 g/L (solid circle). Glucose 4 g/L, sucrose 20 g/L (star). Glucose 2 g/L, sucrose 16 g/L (open circle).
Figure 6B:
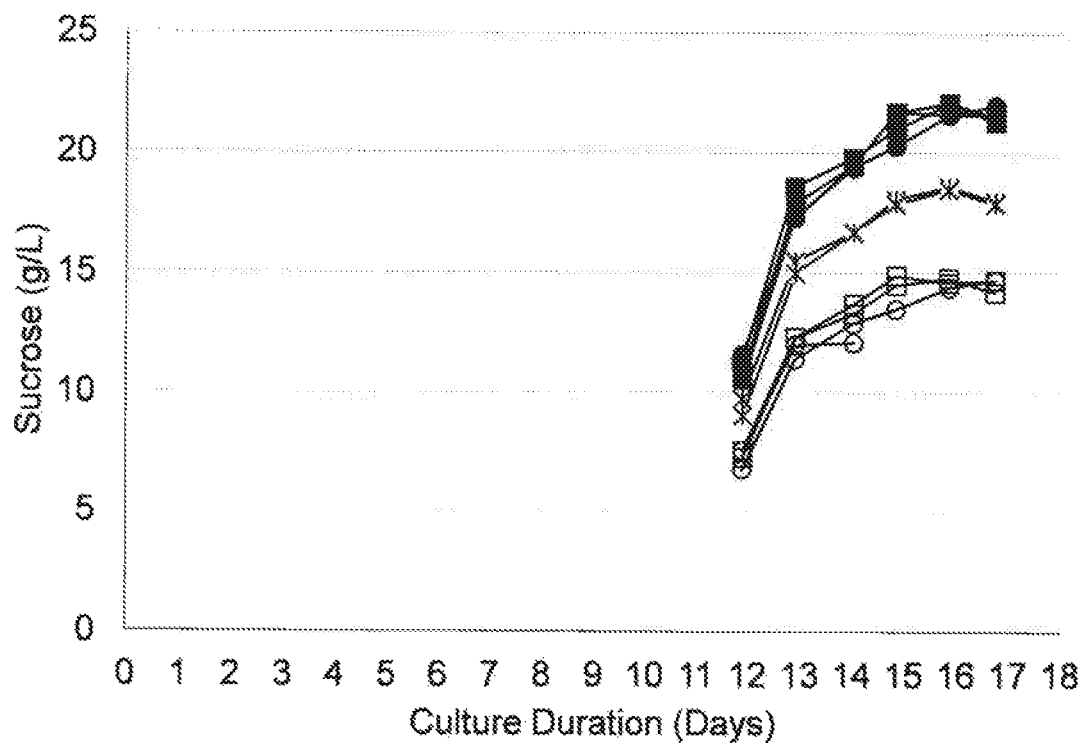

FIG. 6A shows all cell cultures conditions achieved a limited glucose state on day 12. The sucrose levels determined by spent media assay showed that sucrose was essentially unchanged from the concentration in the cell culture medium (FIG. 6B). The 1 g/L difference between the concentration of sucrose in the perfusion medium and in the spent medium was derived from sucrose assay variability and dilution effect. This data indicated that sucrose was not catabolized by CHO cells. Sucrose functions as a hyperosmomatic stress in cell culture that could impact protein glycosylation, see Schmelzer and Miller, Biotechnol. Prog. (2002) 18:346-353; Schmelzer and Miller Biotechnol. Bioeng (2002) 77 (4) February 15; U.S. Pat. No. 8,354,105.

Figure 6C:
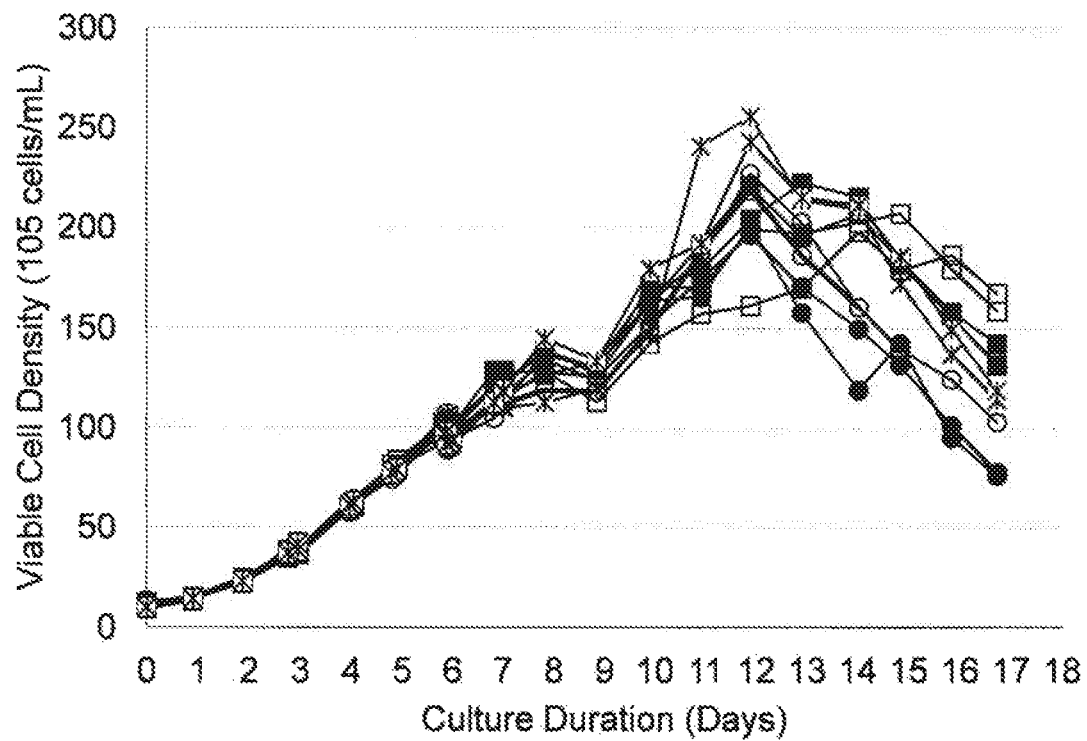
Figure 6D:
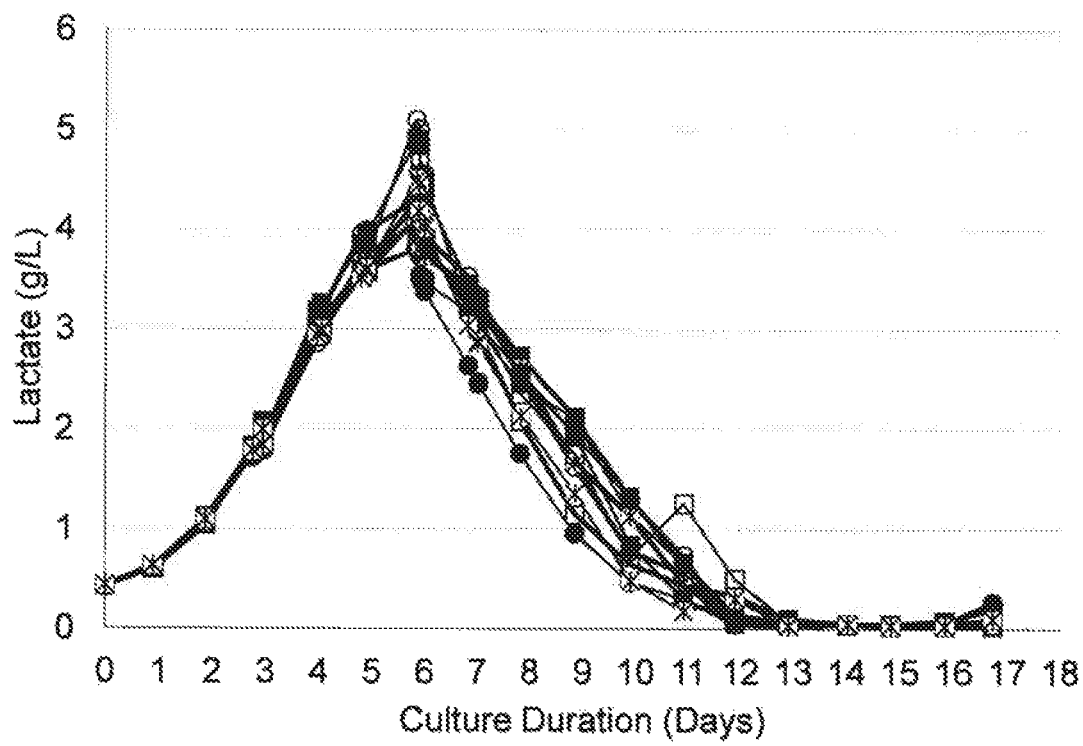
Figure 6E:
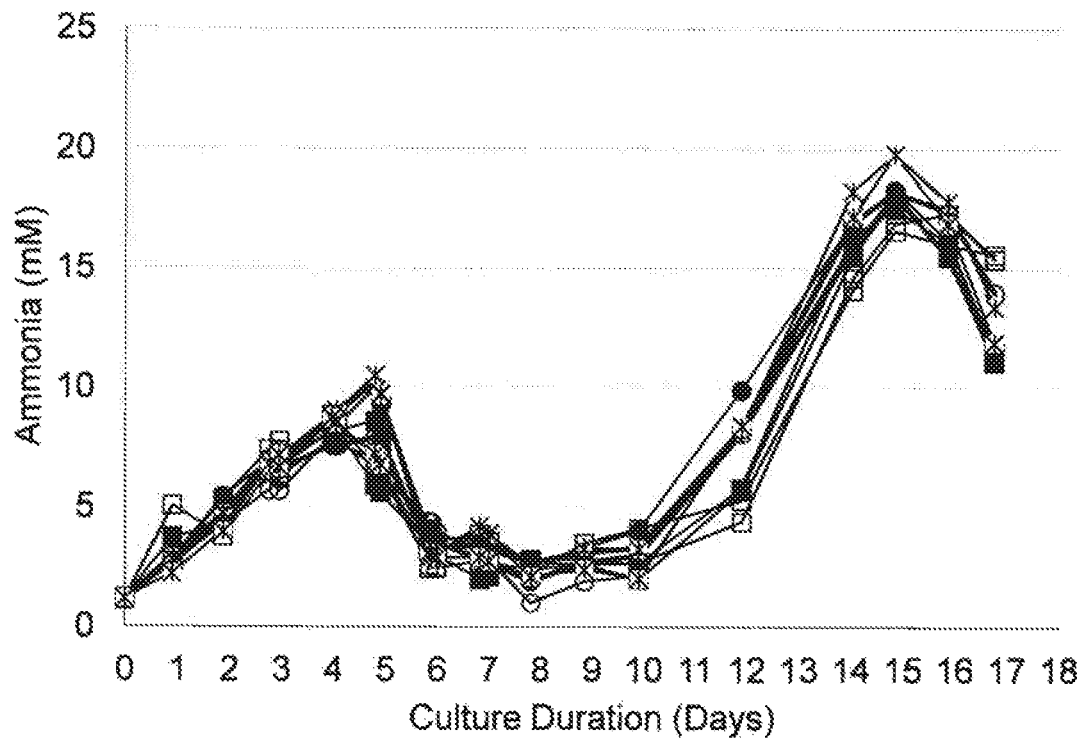
Figure 6F:
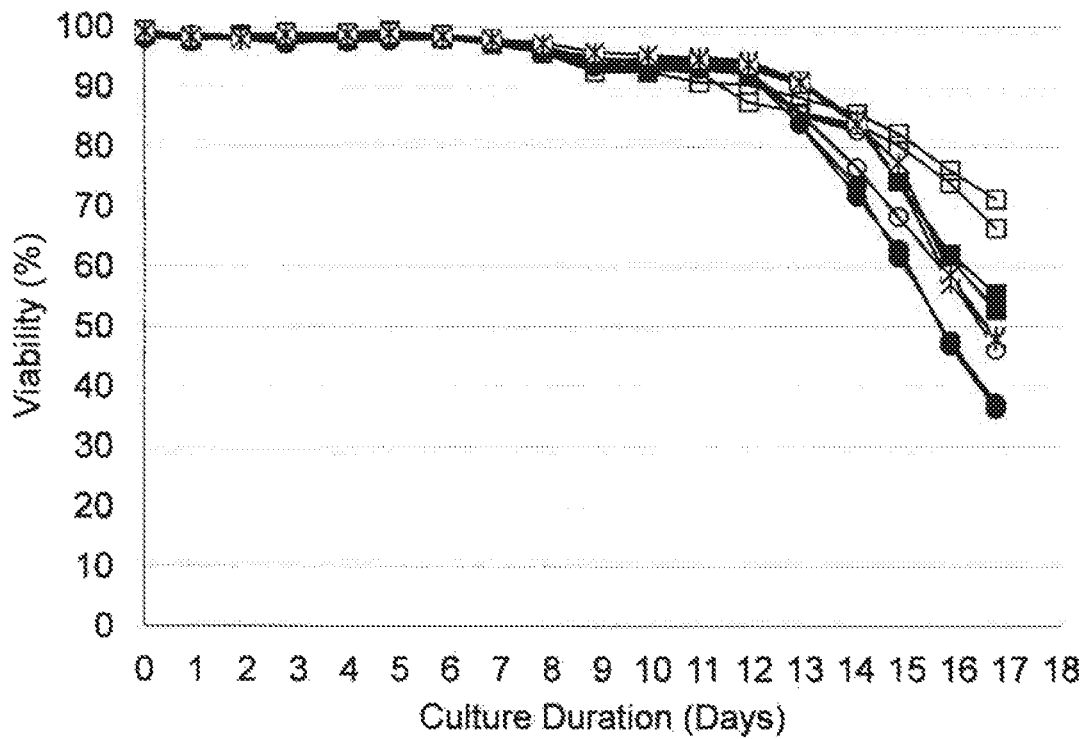
Figure 6G:
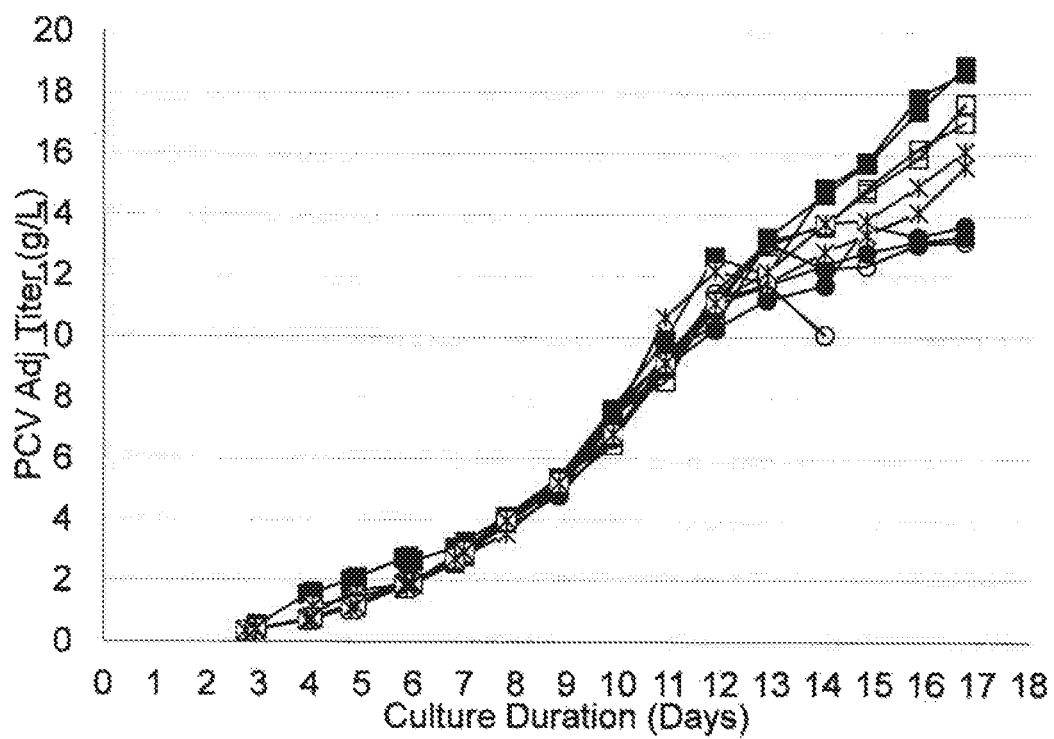

The slight increase in viable cell density, viability and titer resulted from the increase in glucose concentration from 2 to 6 g/L in perfusion medium (FIGS. 6C, 6D and 6F). Lactate levels dipped to zero once the glucose reached limitation on day 12 (FIG. 6G). The ammonia level increased starting on day 11 after glucose reached limitation and sucrose was added (FIG. 6E).

Figure 7A:
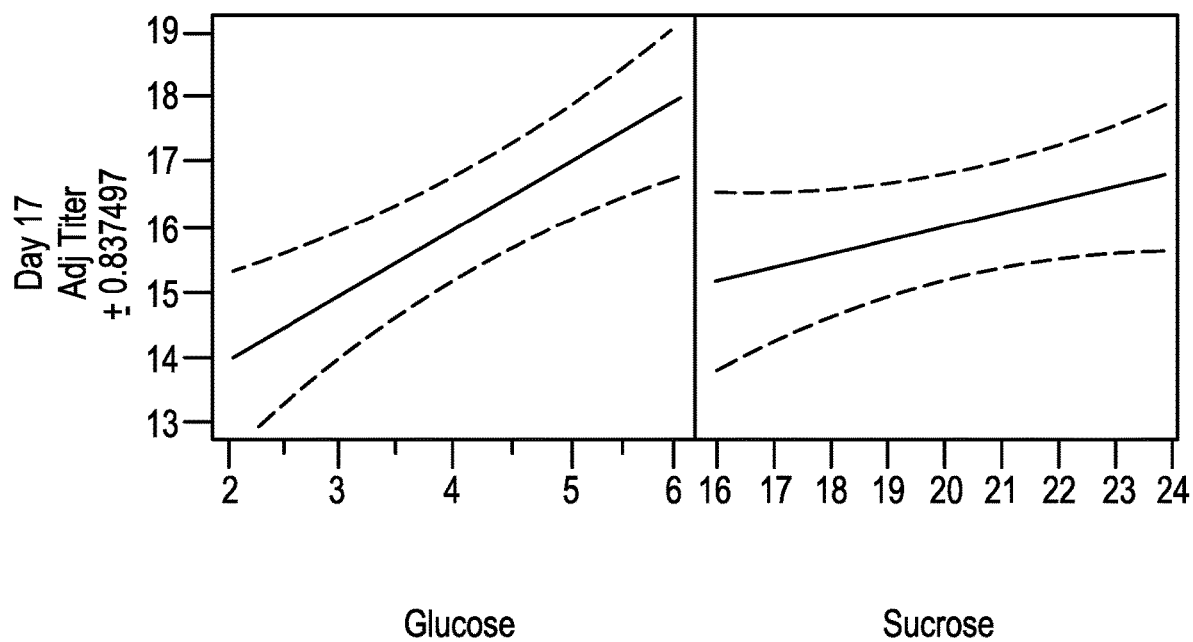
FIG. 7. JMP statistical analysis of perfusion process. (A) Packed Cell Volume Adjusted Titer, (B) Man5, (C) Viability.
Figure 7B:
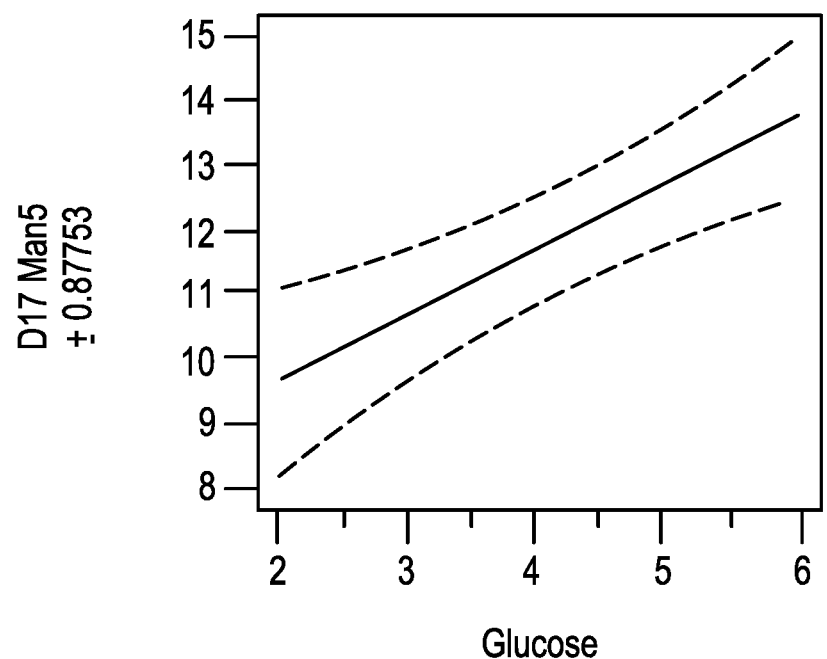

The statistical analysis using JMP software (JMP Inc. Cary, N.C.) revealed that both glucose concentration (p value=0.0021) and sucrose (p value=0.0823) were statistically significant factors that impacted titer (FIG. 7A). The impact of glucose was most significant (FIG. 7B); the impact of sucrose on titer could be as a result of osmolality stress (Schmelzer and Miller, supra; U.S. Pat. No. 8,354,105).

Figure 7C:
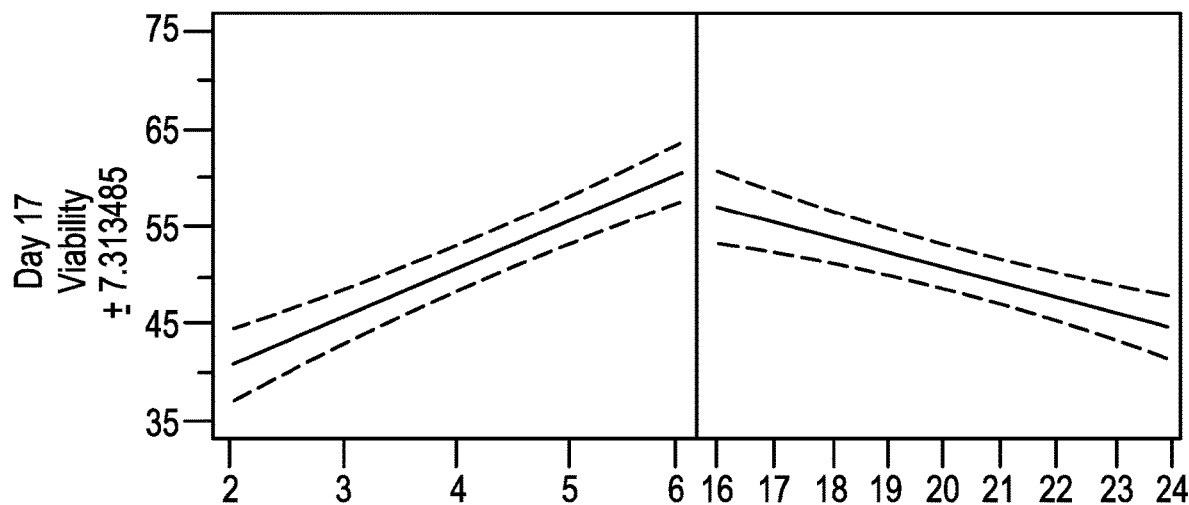

Both glucose concentration (p value=0.001) and sucrose (p value=0.0012) were statistically significant factors that impacted viability (FIG. 7C). Higher glucose concentrations improved viability while higher sucrose concentrations reduced viability. Glucose was the only statistically significant factor that impacted Man5 species (p value=0.019). Overall the Man5 levels were increased when the glucose concentration in the cell culture medium ranged from 2 to 6 g/L.

What is claimed is:

1. A method for modulating mannose 5 on a recombinant protein during a mammalian cell culture process comprising:
    establishing a cell culture of mammalian cells in a bioreactor, wherein the mammalian cells produce a recombinant protein;
    limiting the amount of glucose in the bioreactor, wherein the concentration of the glucose in the spent medium of the bioreactor is from about 0 to 3 g/L;
    and supplementing the cell culture with a feeding medium comprising galactose or sucrose, such that the concentration of galactose in the resulting spent medium of the bioreactor is from 4 g/L to 8 g/L, or the concentration of sucrose in the resulting spent medium of the bioreactor is from about 16-24 g/L.

2. The method according to claim 1, comprising feeding the cell culture with a feeding medium, wherein the glucose concentration in the feeding medium is sufficient to result in a concentration of glucose in the spent medium at about 0 g/L.

3. The method according to claim 1, comprising feeding the cell culture with a feeding medium comprising 4 to 6 g/L glucose.

4. The method according to claim 1, comprising feeding the cell culture with a feeding medium comprising 1 to 3 g/L glucose.

5. The method according to claim 1, comprising feeding the cell culture with a feeding medium comprising 2 to 3 g/L glucose.

6. The method according to claim 1, comprising feeding the cell culture with a feeding medium comprising 2.5 g/L glucose.

7. The method according to claim 1, comprising feeding the cell culture with a feeding medium comprising 0 g/L glucose.

8. The method according to claim 1, comprising feeding the cell culture with a feeding medium comprising 10 to 13 g/L galactose.

9. The method according to claim 1, comprising feeding the cell culture with a feeding medium comprising 10 to 12 g/L galactose.

10. The method according to claim 1, comprising feeding the cell culture with a feeding medium comprising 11.5 g/L galactose.

11. The method according to claim 1, wherein a feeding medium comprising a limiting amount of glucose is fed during a production phase.

12. The method according to claim 1, wherein the cell culture process is a perfusion process.

13. The method according to claim 1, wherein the mammalian cells are Chinese Hamster Ovary (CHO) cells.

14. The method of claim 1, wherein the recombinant protein is selected from the group consisting of a human antibody, a humanized antibody, a chimeric antibody, a recombinant fusion protein and a cytokine.

15. The method according to claim 1, further comprising a step of harvesting the recombinant protein produced by the cell culture.

16. The method of claim 15, wherein the recombinant protein produced by the cell culture is purified and formulated in a pharmaceutically acceptable formulation.

17. The method of claim 1, wherein recombinant protein production in the high mannose glycan species are increased compared to a culture where the cells are not subjected to limited glucose in combination with galactose.

18. The method of claim 1, comprising feeding the cell culture with a feeding medium comprising 6-13 g/L galactose.

19. The method of claim 1, comprising feeding the cell culture with a feeding medium comprising 0 to 6 g/L glucose.

20. A method for modulating mannose 5 on a recombinant protein during a mammalian cell culture process comprising:
    establishing a cell culture of mammalian cells in a bioreactor, wherein the mammalian cells produce a recombinant protein;
    limiting the amount of glucose in the bioreactor, wherein the concentration of the glucose in the spent medium of the bioreactor is from about 0 to 3 g/L;
    and supplementing the cell culture with a feeding medium comprising galactose, such that the concentration of galactose in the resulting spent medium of the bioreactor is above 2.5 g/L.

21. The method of claim 20, wherein the concentration of galactose in the resulting spent medium is from 4 to 8 g/L.

22. The method of claim 20, wherein the concentration of galactose in the resulting spent medium is above 4 g/L.

23. The method of claim 20, comprising feeding the cell culture with a feeding medium comprising 6-13 g/L galactose.

* * * * *